(12) United States Patent
Dutreix et al.

(10) Patent No.: US 8,093,366 B2
(45) Date of Patent: *Jan. 10, 2012

(54) DBAIT AND STANDALONE USES THEREOF

(75) Inventors: Marie Dutreix, L'Hay-les-Roses (FR); Jian-Sheng Sun, Saint Maur des Fosses (FR)

(73) Assignees: Centre National de la Recherche Scientifique, Paris (FR); Institut Curie, Paris (FR); Museum National d'Histoire Naturelle (MNHN), Paris (FR); Institut National de la Sante et de la Recherche Medicale, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/520,961

(22) PCT Filed: Jan. 11, 2008

(86) PCT No.: PCT/EP2008/050265
§ 371 (c)(1),
(2), (4) Date: Jun. 23, 2009

(87) PCT Pub. No.: WO2008/084087
PCT Pub. Date: Jul. 17, 2008

(65) Prior Publication Data
US 2010/0022622 A1    Jan. 28, 2010

(30) Foreign Application Priority Data

Jan. 12, 2007   (EP) .................................. 07300728

(51) Int. Cl.
*C07H 21/04* (2006.01)
*A61K 31/70* (2006.01)
(52) U.S. Cl. ........................................ 536/23.1; 514/44
(58) Field of Classification Search ........................ None
See application file for complete search history.

(56) References Cited

FOREIGN PATENT DOCUMENTS

WO    WO 2005/040378    5/2005

OTHER PUBLICATIONS

Zhang, L. et al. "Targeting Ku protein fro sensitizizng of breast cancer cells to DNA-damage" *International Journal of Molecular Medicine*, 2004, pp. 153-159, vol. 14, XP-008084143.

Yoo, S. et al. "Characterization of the RNA Binding Properties of Ku Protein" *Biochemistry*, 1998, pp. 1336-1343, vol. 37, XP-002452541.

*Primary Examiner* — Tracy Vivlemore
(74) *Attorney, Agent, or Firm* — Saliwanchik, Lloyd & Eisenschenk

(57) ABSTRACT

The invention relates to compositions and methods for interfering with the DNA repair of double strand breaks (DSBs). The invention discloses double-stranded nucleic acid molecules that act as baits and hijack the holocomplex of enzymes responsible for DNA DSB sensing, signaling and/or repair pathways, in particular the non-homologous end joining (NHEJ) pathway of DSB repair. The invention discloses the use of these molecules as a standalone anticancer drug in an efficient amount to be introduced in the tumor cell nuclei in order to trigger their death.

20 Claims, 4 Drawing Sheets

SEQUENCE LISTING

```
<160> NUMBER OF SEQ ID NOS: 31

<210> SEQ ID NO 1
<211> LENGTH: 32
<212> TYPE: DNA
<213> ORGANISM: artificial sequence
<220> FEATURE:
<223> OTHER INFORMATION: Dbait32
<220> FEATURE:
<221> NAME/KEY: misc_feature
<223> OTHER INFORMATION: /note="at the  5' and 3' ends of the
      complementary strand the three last nucleotides with
      phosphorothioate backbone"
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: modified_base
<222> LOCATION: (30)..(32)
<223> OTHER INFORMATION: mod_base=phosphorothioate backbone

<400> SEQUENCE: 1
acgcacgggt gttgggtcgt ttgttcggat ct                                    32

<210> SEQ ID NO 2
<211> LENGTH: 68
<212> TYPE: DNA
<213> ORGANISM: artificial sequence
<220> FEATURE:
<223> OTHER INFORMATION: Dbait32-T4
<220> FEATURE:
<221> NAME/KEY: misc_feature
<223> OTHER INFORMATION: /note="at the 3' end of the complementary
      strand the three last nucleotides with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (33)..(36)
<223> OTHER INFORMATION: loop

<400> SEQUENCE: 2
acgcacgggt gttgggtcgt ttgttcggat cttttagat ccgaacaaac gacccaacac      60
ccgtgcgt                                                              68
```

```
<210> SEQ ID NO 3
<211> LENGTH: 32
<212> TYPE: DNA
<213> ORGANISM: artificial sequence
<220> FEATURE:
<223> OTHER INFORMATION: Dbait 32H-po
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop=hexaethyleneglycol linker

<400> SEQUENCE: 3
acgcacgggt gttgggtcgt ttgttcggat ct                                    32

<210> SEQ ID NO 4
<211> LENGTH: 32
<212> TYPE: DNA
<213> ORGANISM: artificial sequence
<220> FEATURE:
<223> OTHER INFORMATION: Dbait32H
<220> FEATURE:
<221> NAME/KEY: misc_feature
<223> OTHER INFORMATION: /note="at the 3' end of the complementary
      strand the three last nucleotides with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (32)..(32)
<223> OTHER INFORMATION: loop=hexaethyleneglycol linker

<400> SEQUENCE: 4
acgcacgggt gttgggtcgt ttgttcggat ct                                    32

<210> SEQ ID NO 5
<211> LENGTH: 24
<212> TYPE: DNA
<213> ORGANISM: artificial sequence
<220> FEATURE:
<223> OTHER INFORMATION: Dbait24H
<220> FEATURE:
<221> NAME/KEY: misc_feature
<223> OTHER INFORMATION: /note="at the 3' end of the complementary
      strand the three last nucleotides with phosphorothioate backbone"
<220> FEATURE:
<221> NAME/KEY: stem_loop
<222> LOCATION: (1)..(24)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (24)..(24)
<223> OTHER INFORMATION: loop=hexaethyleneglycol linker

<400> SEQUENCE: 5
acgcacgggt gttgggtcgt ttgt                                             24

<210> SEQ ID NO 6
<211> LENGTH: 16
<212> TYPE: DNA
<213> ORGANISM: artificial sequence
<220> FEATURE:
```

```
<223> OTHER INFORMATION: Dbait16H
<220> FEATURE:
<221> NAME/KEY: misc_feature
<223> OTHER INFORMATION: /note="at the 3' end of the complementary
      strand the three last nucleotides with phosphorothioate backbone"
<220> FEATURE:
<221> NAME/KEY: stem_loop
<222> LOCATION: (1)..(16)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (16)..(16)
<223> OTHER INFORMATION: loop= hexaethyleneglycol linker

<400> SEQUENCE: 6
acgcacgggt gttggg                                              16

<210> SEQ ID NO 7
<211> LENGTH: 8
<212> TYPE: DNA
<213> ORGANISM: artificial sequence
<220> FEATURE:
<223> OTHER INFORMATION: Dbait8H
<220> FEATURE:
<221> NAME/KEY: misc_feature
<223> OTHER INFORMATION: /note:"at the 3' end of the complementary
      strand the three last nucleotides with phosphorothioate backbone"
<220> FEATURE:
<221> NAME/KEY: stem_loop
<222> LOCATION: (1)..(8)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (8)..(8)
<223> OTHER INFORMATION: loop= hexaethyleneglycol linker

<400> SEQUENCE: 7 acgcacgg                                                        8

<210> SEQ ID NO 8
<211> LENGTH: 32
<212> TYPE: DNA
<213> ORGANISM: artificial sequence
<220> FEATURE:
<223> OTHER INFORMATION: Dbait32Ha
<220> FEATURE:
<221> NAME/KEY: misc_feature
<223> OTHER INFORMATION: /note= at the 3' end of the complementary
      strain the three last nucleotides with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (32)..(32)
<223> OTHER INFORMATION: loop= hexaethyleneglycol linker

<400> SEQUENCE: 8
cgtaggtctg tttggtggct ttgcagtggc ac                            32

<210> SEQ ID NO 9
<211> LENGTH: 32
<212> TYPE: DNA
<213> ORGANISM: artificial sequence
```

```
<220> FEATURE:
<223> OTHER INFORMATION: Dbait32Hb
<220> FEATURE:
<221> NAME/KEY: misc_feature
<223> OTHER INFORMATION: /note="at the 3'end of the complementary strand
      the three last nucleotides with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (32)..(32)
<223> OTHER INFORMATION: loop= hexaethyleneglycol linker

<400> SEQUENCE: 9
gctaggcttg tttgctgggt tgtaggcaca gc                                32

<210> SEQ ID NO 10
<211> LENGTH: 32
<212> TYPE: DNA
<213> ORGANISM: artificial sequence
<220> FEATURE:
<223> OTHER INFORMATION: Dbait32Hc
<220> FEATURE:
<221> NAME/KEY: misc_feature
<223> OTHER INFORMATION: loop=hexaethyleneglycol linker
<220> FEATURE:
<221> NAME/KEY: misc_feature
<223> OTHER INFORMATION: /note= "at the 3'end of the complementary
      strand the three last nucleotides with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate backbone

<400> SEQUENCE: 10
gctgtgccca caacccagca aacaagccta ga                                32

<210> SEQ ID NO 11
<211> LENGTH: 32
<212> TYPE: DNA
<213> ORGANISM: artificial sequence
<220> FEATURE:
<223> OTHER INFORMATION: Dbait32Hd
<220> FEATURE:
<221> NAME/KEY: misc_feature
<223> OTHER INFORMATION: /note= "at the 3'end of the complementary
      strand the three last nucleotides with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc_feature
<222> LOCATION: (32)..(32)
<223> OTHER INFORMATION: loop= hexaethyleneglycol linker

<400> SEQUENCE: 11
gctaggtctg tttggtggct ttgcagtggc ac                                32

<210> SEQ ID NO 12
<211> LENGTH: 32
<212> TYPE: DNA
<213> ORGANISM: artificial sequence
```

```
-continued

<220> FEATURE:
<223> OTHER INFORMATION: Dbait32Hc-3'mp
<220> FEATURE:
<221> NAME/KEY: misc_feature
<223> OTHER INFORMATION: /note="last 3 nucleotides at the 3'end  of the
      complementary strand  with methylphosphonate linkage"
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop= hexaethyleneglycol linker

<400> SEQUENCE: 12
gctgtgccca caacccagca aacaagccta ga                                    32

<210> SEQ ID NO 13
<211> LENGTH: 32
<212> TYPE: DNA
<213> ORGANISM: artificial sequence
<220> FEATURE:
<223> OTHER INFORMATION: Dbait32Hc-5'3'mp
<220> FEATURE:
<221> NAME/KEY: misc_feature
<223> OTHER INFORMATION: /note= "the three last nucleotides at the 3'end
      of the complementary strand with methylphosphonate linkage"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= methylphosphonate linkage
<220> FEATURE:
<221> NAME/KEY: misc_feature
<222> LOCATION: (32)..(32)
<223> OTHER INFORMATION: loop=hexaethyleneglycol linker

<400> SEQUENCE: 13
gctgtgccca caacccagca aacaagccta ga                                    32

<210> SEQ ID NO 14
<211> LENGTH: 32
<212> TYPE: DNA
<213> ORGANISM: artificial sequence
<220> FEATURE:
<223> OTHER INFORMATION: Dbait32Hc-5'5'
<220> FEATURE:
<221> NAME/KEY: misc_feature
<223> OTHER INFORMATION: /note= "the last nucleotide at the 3'end of the
      complementary strand is linked with 3'-3'linkage"
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop=hexaethyleneglycol linker

<400> SEQUENCE: 14
gctaggcttg tttgctgggt tgtaggcaca gc                                    32

<210> SEQ ID NO 15
<211> LENGTH: 32
<212> TYPE: DNA
<213> ORGANISM: artificial sequence
<220> FEATURE:
<223> OTHER INFORMATION: Dbait32-NH2
<220> FEATURE:
<221> NAME/KEY: misc_feature
<223> OTHER INFORMATION: /note="the  nucleotide at the 5' end of the
      complementary strand is linked to NH2 group"
<220> FEATURE:
```

```
<221> NAME/KEY: misc_feature
<223> OTHER INFORMATION: /note= "the three last nucleotides at the
      3'end of the complementary strand with phosphorothioate backbone"
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc_binding
<222> LOCATION: (32)..(32)
<223> OTHER INFORMATION: linker= NH2

<400> SEQUENCE: 15
acgcacgggt gttgggtcgt tgttcggat ct                                      32

<210> SEQ ID NO 16
<211> LENGTH: 32
<212> TYPE: DNA
<213> ORGANISM: artificial sequence
<220> FEATURE:
<223> OTHER INFORMATION: Dbait32C
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: loop=hexaethyleneglycol linker
<220> FEATURE:
<221> NAME/KEY: misc_feature
<222> LOCATION: (32)..(32)
<223> OTHER INFORMATION: loop=hexaethyleneglycol linker

<400> SEQUENCE: 16
acgcacgggt gttgggtcgt tgttcggat ct                                      32

<210> SEQ ID NO 17
<211> LENGTH: 32
<212> TYPE: DNA
<213> ORGANISM: artificial sequence
<220> FEATURE:
<223> OTHER INFORMATION: Dbait32ss
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: modified_base
<222> LOCATION: (30)..(32)
<223> OTHER INFORMATION: mod_base=phosphorothioate backbone

<400> SEQUENCE: 17
acgcacgggt gttgggtcgt tgttcggat ct                                      32

<210> SEQ ID NO 18
<211> LENGTH: 32
<212> TYPE: DNA
<213> ORGANISM: artificial sequence
<220> FEATURE:
<223> OTHER INFORMATION: Dbait32Hcss-po

<400> SEQUENCE: 18
gctgtgccca aacccagca aacaagccta ga                                      32

<210> SEQ ID NO 19
<211> LENGTH: 64
<212> TYPE: DNA
<213> ORGANISM: artificial sequence
<220> FEATURE:
<223> OTHER INFORMATION: Dbait64
<220> FEATURE:
<221> NAME/KEY: misc_feature
```

```
<223> OTHER INFORMATION: /note= "the three last nucleotides at the 3'
      end of the complementary strand with phosphorothioate backbone"
<220> FEATURE:
<221> NAME/KEY: misc_feature
<223> OTHER INFORMATION: /note= "the three nucleotides at the 5' end of
      the complementary strand with phosphorothioate backbone"
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: modified_base
<222> LOCATION: (62)..(64)
<223> OTHER INFORMATION: mod_base=phosphorothioate backbone

<400> SEQUENCE: 19
acgcacgggt gttgggtcgt tgttcggat ctacgcacgg tcgtttgttc ggtgttggcg     60
atct                                                                64

<210> SEQ ID NO 20
<211> LENGTH: 63
<212> TYPE: DNA
<213> ORGANISM: Artificial
<220> FEATURE:
<223> OTHER INFORMATION: Dbait64-L
<220> FEATURE:
<221> NAME/KEY: misc_feature
<223> OTHER INFORMATION: /note= "the three last nucleotides at the 3'end
      of the complementary strand with phosphorothioate backbone"
<220> FEATURE:
<221> NAME/KEY: misc_feature
<223> OTHER INFORMATION: /note= "the three nucleotides at the 5' end of
      the complementary strand with phosphorothioate backbone"
<220> FEATURE:
<221> NAME/KEY: modified_base
<222> LOCATION: (1)..(3)
<223> OTHER INFORMATION: mod_base= hexaethyleneglycol linker
<220> FEATURE:
<221> NAME/KEY: repeat_region
<222> LOCATION: (32)..(33)
<223> OTHER INFORMATION: rpt_type= hexaethyleneglycol linker
<220> FEATURE:
<221> NAME/KEY: modified_base
<222> LOCATION: (61)..(63)
<223> OTHER INFORMATION: mod_base= hexaethyleneglycol linker

<400> SEQUENCE: 20
acgcacgggt gttgggtcgt tgttcggat cacgcacggt cgtttgttcg gtgttggcga     60
tct                                                                 63

<210> SEQ ID NO 21
<211> LENGTH: 32
<212> TYPE: DNA
<213> ORGANISM: Artificial
<220> FEATURE:
<223> OTHER INFORMATION: Dbait32H-FITC
<220> FEATURE:
<221> NAME/KEY: misc_feature
<223> OTHER INFORMATION: /note= "the three last nucleotides at the 3'end
      of the complementary strand with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base=phosphorothioate backbone
<220> FEATURE:
<221> NAME/KEY: misc_feature
<222> LOCATION: (32)..(32)
<223> OTHER INFORMATION: loop= hexaethyleneglycol linker
<220> FEATURE:
<221> NAME/KEY: misc-binding
<222> LOCATION: (32)..(32)
```

```
<223> OTHER INFORMATION: linker=FITC

<400> SEQUENCE: 21
acgcacgggt gttgggtcgt ttgttcggat ct                                    32

<210> SEQ ID NO 22
<211> LENGTH: 32
<212> TYPE: DNA
<213> ORGANISM: Artificial
<220> FEATURE:
<223> OTHER INFORMATION: Dbait32H-Cy3
<220> FEATURE:
<221> NAME/KEY: misc_feature
<223> OTHER INFORMATION: /note= "the three last nucleotides at the 3'
      end of the complementary strand with phosphorothioate backbone"
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop= hexaethyleneglycol linker
<220> FEATURE:
<221> NAME/KEY: misc-binding
<222> LOCATION: (32)..(32)
<223> OTHER INFORMATION: linker= Cyanine3

<400> SEQUENCE: 22
acgcacgggt gttgggtcgt ttgttcggat ct                                    32

<210> SEQ ID NO 23
<211> LENGTH: 32
<212> TYPE: DNA
<213> ORGANISM: Artificial
<220> FEATURE:
<223> OTHER INFORMATION: Dbait32H-Biot
<220> FEATURE:
<221> NAME/KEY: misc_feature
<223> OTHER INFORMATION: /note= "the three last nucleotides at the 3'
      end of the complementary strand with phosphorothioate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc-binding
<222> LOCATION: (32)..(32)
<223> OTHER INFORMATION: linker= biotine
<220> FEATURE:
<221> NAME/KEY: misc_feature
<222> LOCATION: (32)..(32)
<223> OTHER INFORMATION: loop= hexaethyleneglycol linker

<400> SEQUENCE: 23
acgcacgggt gttgggtcgt ttgttcggat ct                                    32

<210> SEQ ID NO 24
<211> LENGTH: 8
<212> TYPE: DNA
<213> ORGANISM: Artificial
<220> FEATURE:
<223> OTHER INFORMATION: Dbait8Hc-Cy3
<220> FEATURE:
<221> NAME/KEY: misc_feature
<223> OTHER INFORMATION: /note="the nucleotide at the 5' end of the
      complementary strand linked to cyanine 3"
<220> FEATURE:
<221> NAME/KEY: misc_feature
<223> OTHER INFORMATION: /note="the last three nucleotides at the 3'end
      of the complementary strand with phosphorothioate backbone"
<220> FEATURE:
```

```
<221> NAME/KEY: stem_loop
<222> LOCATION: (1)..(8)
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc_feature
<222> LOCATION: (8)..(8)
<223> OTHER INFORMATION: loop= hexaethyleneglycol linker

<400> SEQUENCE: 24 gctgtgca                                                                 8

<210> SEQ ID NO 25
<211> LENGTH: 32
<212> TYPE: DNA
<213> ORGANISM: Artificial
<220> FEATURE:
<223> OTHER INFORMATION: Dbait32Hc-Cy3
<220> FEATURE:
<221> NAME/KEY: misc_feature
<223> OTHER INFORMATION: /note= "the last three nucleotides at the 3'end
      of the complementary strand with phosphorothioate backbone"
<220> FEATURE:
<221> NAME/KEY: misc_feature
<223> OTHER INFORMATION: /note= "the nucleotide at the 5'end of the
      complementary strand linked to Cyanine 3"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc_feature
<222> LOCATION: (32)..(32)
<223> OTHER INFORMATION: loop= hexaethyleneglycol linker

<400> SEQUENCE: 25
gctgtgccca aacccagca aacaagccta ga                                       32

<210> SEQ ID NO 26
<211> LENGTH: 32
<212> TYPE: DNA
<213> ORGANISM: Artificial
<220> FEATURE:
<223> OTHER INFORMATION: Dbait32Hc-Cy5
<220> FEATURE:
<221> NAME/KEY: misc_feature
<223> OTHER INFORMATION: /note= "the last three nucleotides at the 3'end
      of the complementary strand with phosphorothioate backbone"
<220> FEATURE:
<221> NAME/KEY: misc_feature
<223> OTHER INFORMATION: /note= "the nucleotide at the 5'end of the
      complementary strand linked to Cyanine-5"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc_feature
<222> LOCATION: (32)..(32)
<223> OTHER INFORMATION: loop= hexaethyleneglycol linker

<400> SEQUENCE: 26
gctgtgccca aacccagca aacaagccta ga                                       32

<210> SEQ ID NO 27
<211> LENGTH: 32
```

-continued

```
<212> TYPE: DNA
<213> ORGANISM: Artificial
<220> FEATURE:
<223> OTHER INFORMATION: Dbait32Hd-FITC
<220> FEATURE:
<221> NAME/KEY: misc_feature
<223> OTHER INFORMATION: /note= "the last three nucleotides at the 3'end
      of the complementary strand with phosphorothioate backbone"
<220> FEATURE:
<221> NAME/KEY: misc_feature
<223> OTHER INFORMATION: /note= "the second nucleotide from the 5'end of
      the complementary strand linked to FITC"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate backbone
<220> FEATURE:
<221> NAME/KEY: misc_feature
<222> LOCATION: (32)..(32)
<223> OTHER INFORMATION: loop= hexaethyleneglycol linker

<400> SEQUENCE: 27
gctaggtctg tttggtggct tgcagtggc ac                                32

<210> SEQ ID NO 28
<211> LENGTH: 32
<212> TYPE: DNA
<213> ORGANISM: artificial sequence
<220> FEATURE:
<223> OTHER INFORMATION: Dbait32Ha ds

<400> SEQUENCE: 28
cgtaggtctg tttggtggct tgcagtggc ac                                32

<210> SEQ ID NO 29
<211> LENGTH: 32
<212> TYPE: DNA
<213> ORGANISM: artificial sequence
<220> FEATURE:
<223> OTHER INFORMATION: Dbait32Hb ds

<400> SEQUENCE: 29
gctaggcttg tttgctgggt tgtaggcaca gc                               32

<210> SEQ ID NO 30
<211> LENGTH: 32
<212> TYPE: DNA
<213> ORGANISM: artificial sequence
<220> FEATURE:
<223> OTHER INFORMATION: Dbait32Hc ds

<400> SEQUENCE: 30
gctgtgccca cacccagca acaagccta ga                                 32

<210> SEQ ID NO 31
<211> LENGTH: 32
<212> TYPE: DNA
<213> ORGANISM: artificial sequence
<220> FEATURE:
<223> OTHER INFORMATION: Dbait32Hd ds

<400> SEQUENCE: 31
gctaggtctg tttggtggct tgcagtggc ac                                32
```

DBAIT AND STANDALONE USES THEREOF

CROSS-REFERENCE TO RELATED APPLICATION

Figure 1:
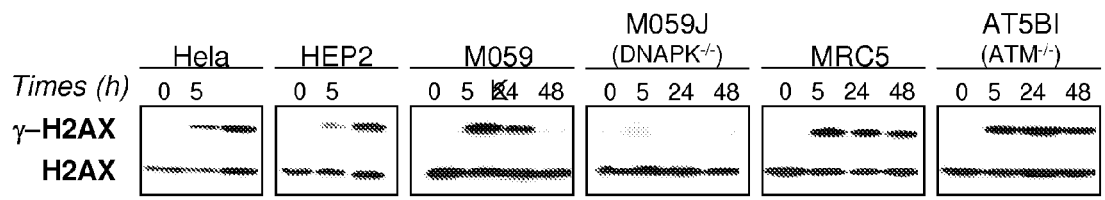

This application is the U.S. national stage application of International Patent Application No. PCT/EP2008/050265, filed Jan. 11, 2008, the disclosure of which is hereby incorporated by reference in its entirety, including all figures, tables and amino acid or nucleic acid sequences.

This invention relates to compositions and methods of interfering with DNA double strand break repair pathways in mammalian cells. Accordingly, the invention relates to compositions and methods for treating proliferative disorders.

BACKGROUND

Radiotherapy and chemotherapy, alone or combined together with surgery, are essential therapeutic arsenals against human cancer. The association between chemotherapy and radiotherapy was widely used in cancer treatment. Although still not completely elucidated, the biological basis of action of the cytotoxics relies on cellular mechanisms, such as cell cycle or DNA damage, which is also important for the radio-induced cell death, leading to the additive or even better synergistic benefits by combining different treatments in cancer therapies.

Recent progress in developing biological drugs (monoclonal antibodies, cytokines/kinase inhibitors, immunotherapies/vaccines) has proven their efficiency and specificity towards a subset of tumors. But they are often used in combination with chemical cytotoxics. Despite of many progresses in the development of new cytotoxic drugs, the drug resistance to chemotherapy is still a major clinical concern in the treatment of cancers. The understanding of the mechanism of drug resistance related to drug uptake/efflux, metabolic degradation, mutagenesis of target, enhanced repair, signaling of cell death (apoptosis and necrosis) is essential for ensuring efficiency of chemotherapy and improving therapeutic index, especially, in some treatment-resistant tumors.

In the last decade, many investigations were carried out in this field, and the complexity of signal transduction in response to radiation began to be delineated. In this respect, genes of particular interest to be targeted with ionizing radiations are those involved in the regulation of radiation-induced lethality mechanisms, such as apoptosis or DNA repair. As double-stranded breaks (DSBs) are the most lethal DNA damages, the efficacy of ionizing radiation decreases as that of DSB repair increases.

Two mechanisms are involved in the repair of DSBs: non homologous end-joining (NHEJ, sequence-independent pathway) and homologous recombination (HR, sequence-dependent pathway) (reviewed by Jackson, 2002). Targeting genes involved in these two main DSB repair pathways has so far led to little or moderate radio-sensitivity, depending on the used approaches and cancer cell lines (Belenkov et al., 2002; Marangoni et al. 2000a; Ohnishi et al, 1998).

Ku (e.g., Ku70 and Ku80) and DNA-PKcs proteins are important in the repair of radiation- or chemo-induced DNA DSBs. If damage cannot be repaired on time, cells die. Therefore, they represent potentially interesting molecular targets for sensitizing target cells and tissues to radiotherapy and chemotherapy. Many approaches have thus been conceived and carried out to try to inhibit these key proteins (Ku70/Ku80, DNA-PKcs, etc.) involved in the NHEJ pathway, which is predominant in mammalian cells:

1) Inhibitors of P13K (phosphatidylinositol-3-kinase) (i.e., DNA-PKcs, ATM, ATR) (Bouton et al., 2000; Durant & Karran, 2003; Willmore et al., 2004; Vauger et al., 2004);
2) Negative dominant & peptides (C-terminal of KU80) (Marangoni et al., 2000b; Kim et al., 2002);
3) Single chain antibody variable fragment (scFv) (DNA-PKcs) (Li et al. 2003a);
4) RNA Aptamer (SELEX: RNA binding Ku) (Yoo & Dynan, 1998);
5) Antisense (Ku70,Ku80, DNA-PKcs) (Li et al., 2003b; Marangoni et al., 2000c; Sak et al., 2002);
6) siRNA (DNA-PKcs) (Peng et al. 2000).

Despite these tremendous efforts, the combination of the targeting of genes involved in DNA repair pathways and cancer therapies is still in early experimental stages and no clinical study has shown any proven benefits so far. It is worth to note that the above described approaches share a common feature: they target a single effector (protein) involved in a complex cascade pathway (such as NHEJ) with possible bypass or compensation.

The patent application WO2005/040378 disclosed compositions and methods of interfering with DNA double strand break repair pathways in mammalian cells. Particularly, it relates to nucleic acid molecules that interfere, in a non gene-specific manner, with DNA damage sensing, signaling and/or repair pathways, as well as to their uses for triggering cell lethality of tumors submitted to anticancer therapies. It describes that the sensitivity of cells to direct or indirect DNA damaging therapies can be enhanced by using (chemically modified or not) short dsDNA molecules which act as mimics of broken DNA fragments and are recognized as DSB sites induced by the DNA damaging treatments (i.e. the substrate mimics of DSB). These molecules, also designated by the name of "DSB bait" molecules (Dbait in short), confer or increase sensitivity of any tumor cell to DNA damaging cancer therapy treatment, namely chemotherapy and radiotherapy. Dbait molecules act by baiting and hijacking the holocomplex of DNA DSB repair enzymes, and thereby interfere with DNA lesion sensing, signaling and/or repair processes. Accordingly, this application relates to Dbait molecules in combination with physical and/or chemical agent(s) which can directly or indirectly cause DSBs of DNA.

SUMMARY OF THE INVENTION

The inventors have surprisingly found that tumor cells are sensitive to the presence of Dbait molecules alone, in the absence of any direct or indirect DNA damaging treatment (i.e. chemotherapy, radiotherapy). As shown in the examples, the Dbait molecules are effective in vitro as well as in vivo, to use as a standalone cancer treatment.

Accordingly, the present invention concerns the use of a nucleic acid molecule for preparing a medicament for treating a proliferative disorder in absence of any direct or indirect DNA damaging treatment, wherein said nucleic acid molecule comprises a double stranded portion of at least 16 bp, more than 24 bp, preferably 32 bp, has at least one free end, and wherein said molecule is substrate for binding by at least a Ku protein and is able to activate DNA-PKcs.

The present invention also concerns a method for treating a proliferative disorder in a subject comprising administering to said subject a therapeutically efficient amount of a nucleic acid molecule comprising a double stranded portion of at least 16 bp, preferably 32 bp, having at least one free end, being substrate for binding by at least a Ku protein and being able to activate DNA-PKcs.

The present invention also concerns a method for assessing the efficiency of a treatment with a nucleic acid according to the present invention comprising determining the phosphorylation of histone H2AX.

The present invention further concerns a method for increasing the phosphorylation of histone H2AX or for activating histone H2AX in cells and/or tissue comprising introducing into said cells and/or tissue nucleic acid of the present invention.

LEGENDS OF THE FIGURES

FIG. 1: Western blot of histone H2AX and the phosphorylated histone H2AX (γ-H2AX) in various cell lines derived from human tumors (Hela, Hep2 and MO59K) and from transformed fibroblast (MRC5). MO59J is DNA-PK deficient (derived from wild type MO59K. AT5BI is ATM-deficient (derived from wild type MRC5).

Figure 2:
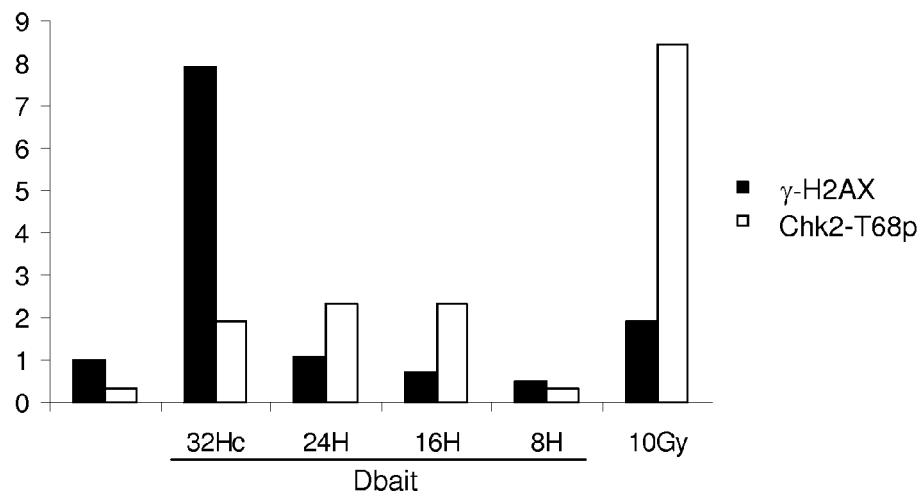

FIG. 2: The level of phosphorylated histone H2AX (γ-H2AX) and phosphorylated check point protein Chk2 (Chk2-T68p) in Hep2 cells 5 hours after transfection by various Dbait molecules, or 1 hour after 10Gy irradiation.

Figure 3:
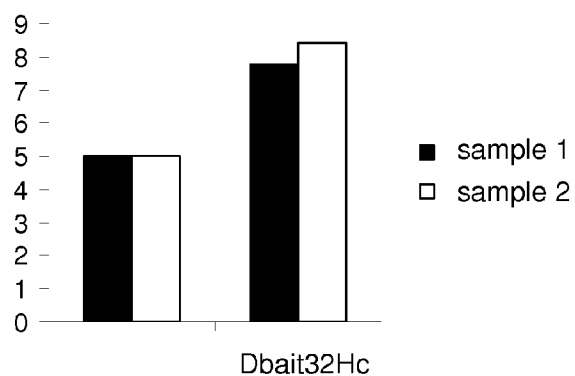

FIG. 3: Western blot analysis of the level of γ-H2AX in Hep2 tumor removal.

Figure 4:
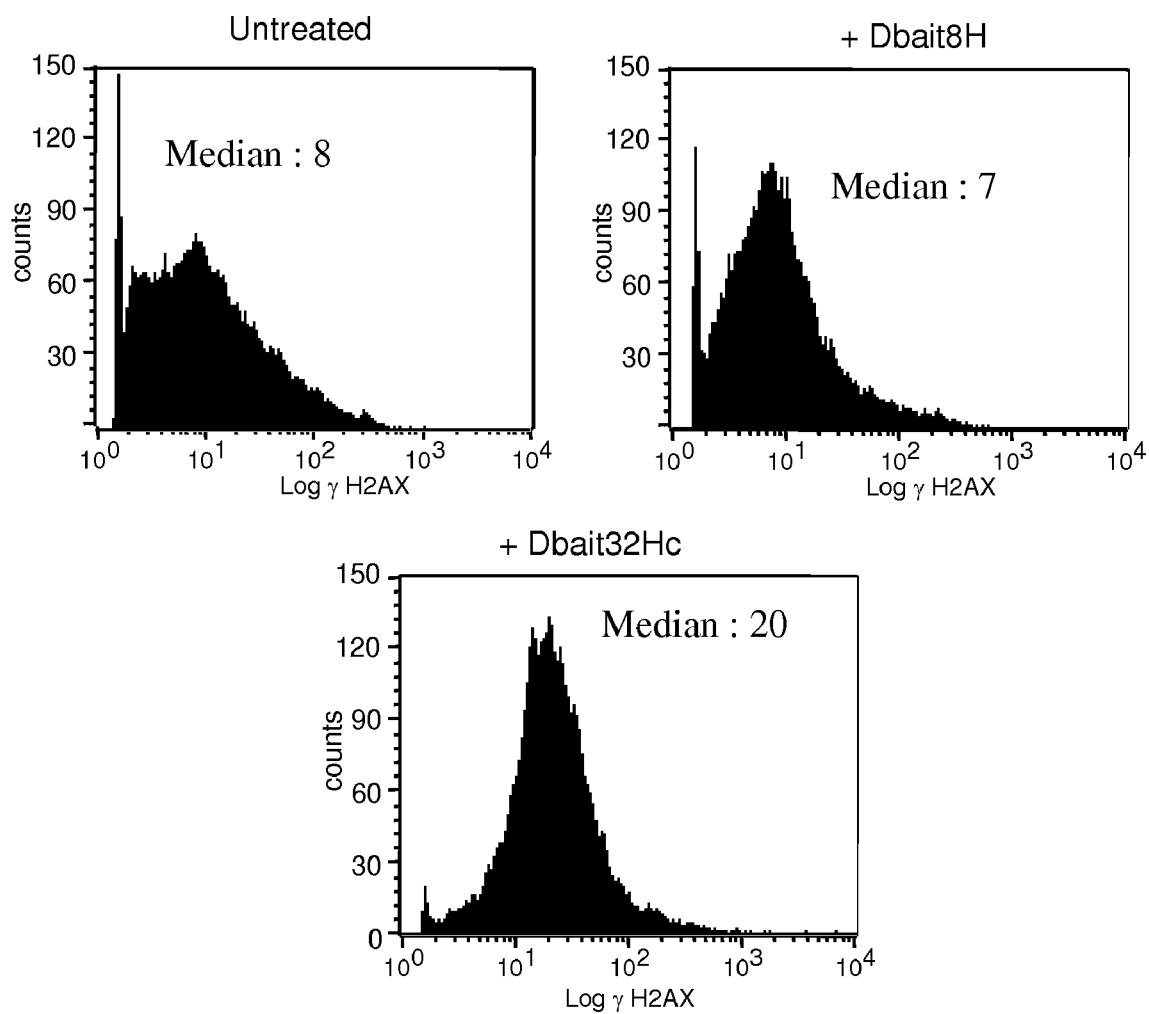

FIG. 4: FASC analysis of the level γ-H2AX in Hep2 tumor removal.

Figure 5:
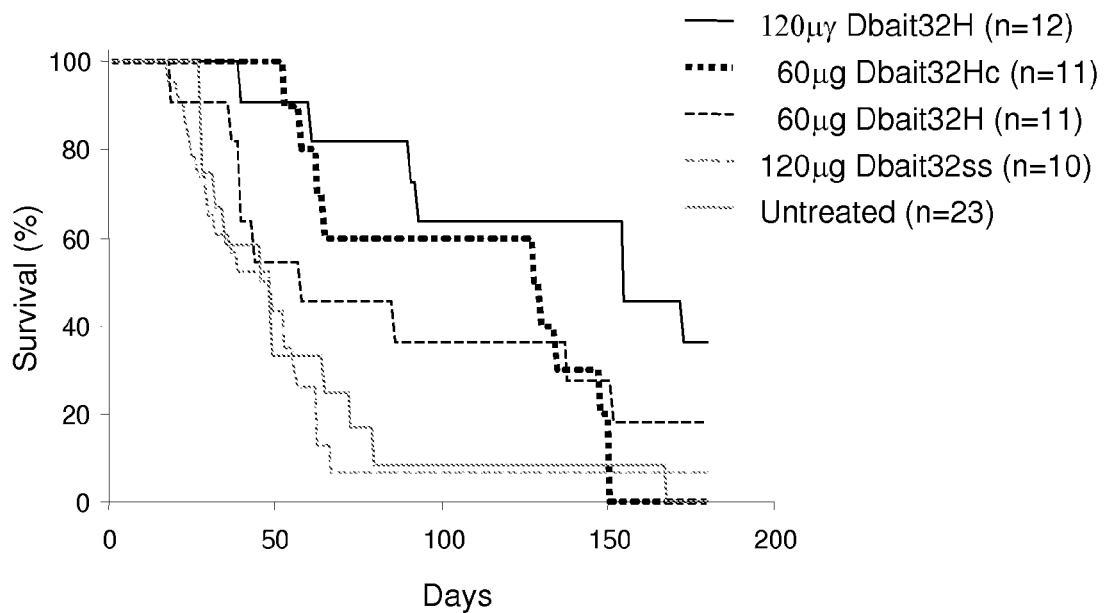

FIG. 5: Kaplan-Meier plot of Hep2 (HNSCC) xenograft on nude mice.

Figure 6:
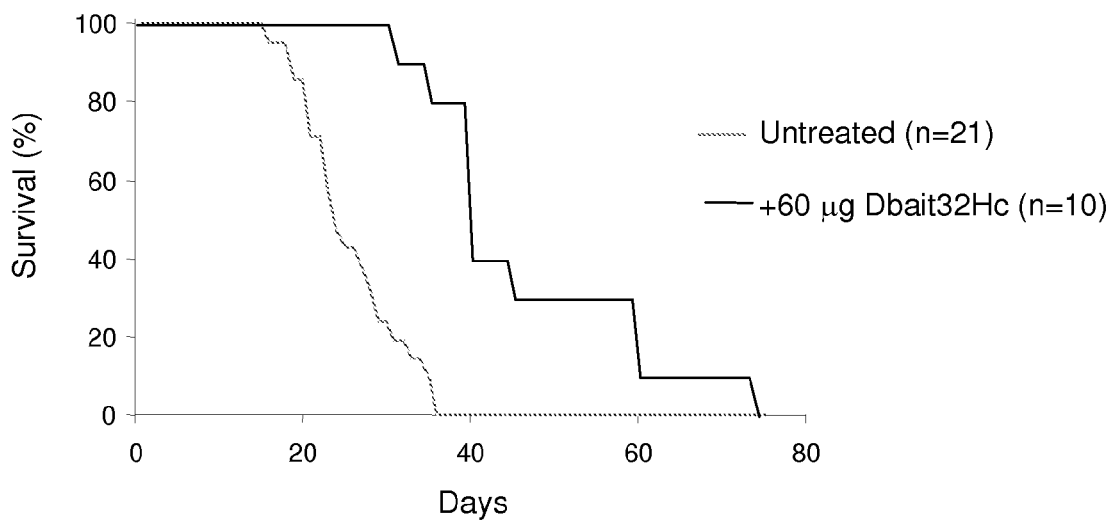

FIG. 6: Kaplan-Meier plot of LU1205 xenograft on nude mice.

Figure 7:
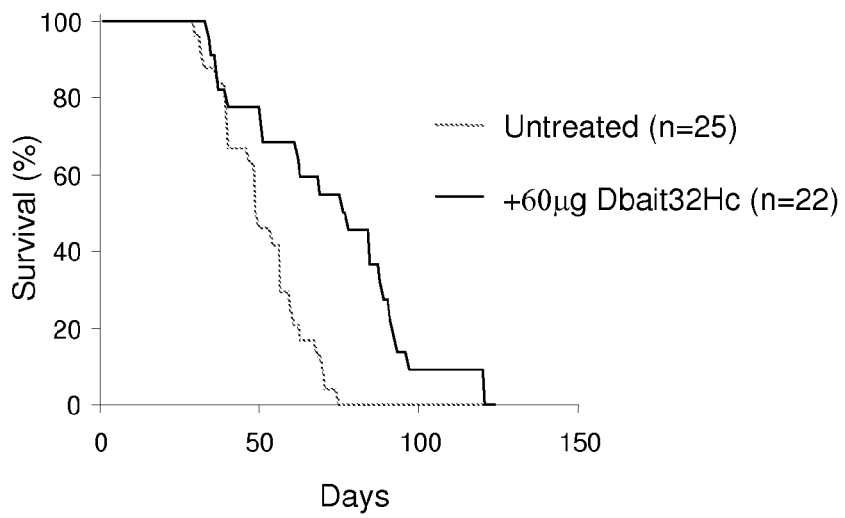

FIG. 7: Kaplan-Meier plot of SK28 xenograft on nude mice.

Figure 8:
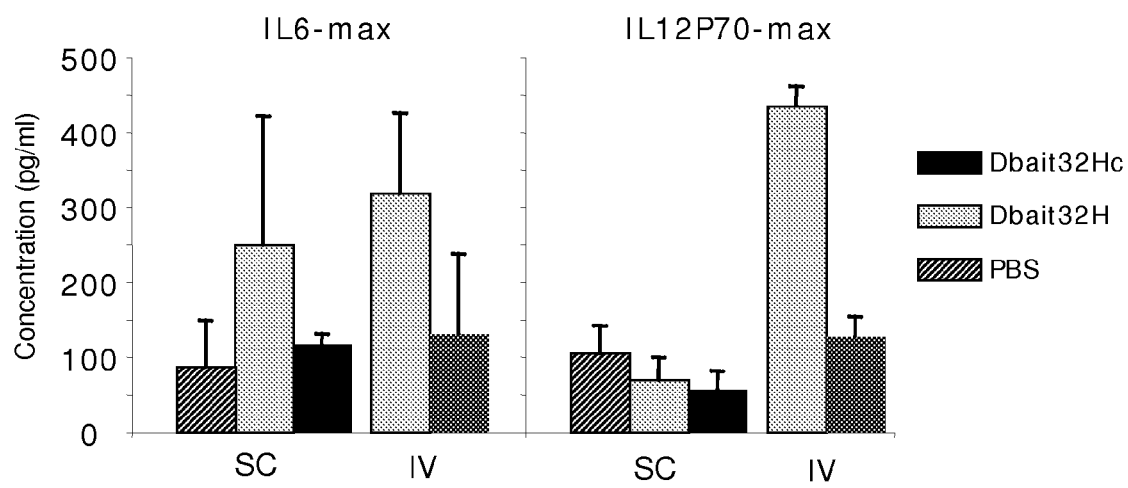

FIG. 8: Immune responses of Dbait injections in Balb/C mice.

DETAILED DESCRIPTION OF THE INVENTION

As disclosed in the patent application WO2005/040378, the Dbait molecules are a novel class of therapeutic molecules which can interfere, in a non gene-specific manner, with DNA DSB repair systems in mammalian cells. These new molecules, termed Dbait molecules, are substrates for the holocomplex of proteins involved in the NHEJ pathway (sequence-independent pathway), particularly Ku and/or DNA-PK proteins, and can neutralize the DNA repair capacity of cells, thereby increasing their sensitivity to DNA damaging treatments.

The present invention further discloses the ability of Dbait molecules to trigger phosphorylation of a key guardian of chromosome integrity, histone H2AX, in the absence of DNA damaging treatment. This post-translational modification of H2AX is mediated by DNA-PK (DNA dependent kinase)-mediated pathway, but is independent of ATM (Ataxia Telangiectasia Mutated)-mediated pathway.

The biological consequence of such unexpectedly/erroneously activation of H2AX is the disorganization of DNA double strand break (DSB) repair systems, in particular the non homologous end joining (NHEJ) pathway, thereby inducing cell lethality in tumor cells which have higher level of spontaneously (replication errors) and endogenously (oxidative stress) occurring DSBs than normal cells.

More particularly, the present invention provides evidence that Dbait molecules are capable of triggering cell/tissue lethality of human tumors xenografted on nude mice, in the absence of any DNA damaging treatment.

Therefore, the present invention thus relates to the use of such molecules as standalone therapeutic agents, particularly for treating proliferative diseases.

Dbait molecules of the present invention may be defined by a number of characteristics, such as their minimal length, the presence of at least one free end, and the presence of a double stranded portion. As will be discussed below, an important feature of Dbait molecules is that their precise nucleotide sequence does not impact substantially on their activity. Furthermore, Dbait molecules may contain a modified and/or non-natural backbone.

The Dbait molecule is preferably of non-human origin (i.e., its nucleotide sequence and/or conformation (e.g., hairpin) does not exist as such in a human cell), most preferably of synthetic origin.

According to the mechanism of action of Dbait molecules, the sequence of the Dbait molecules plays little, if any, role. Accordingly, in contrast with molecules used in the prior art for gene/protein-specific targeting (e.g., antisense, antigene, siRNA, aptamer, decoy, ribozyme, etc.), Dbait molecules may not have any significant degree of sequence homology or identity to known genes, promoters, enhancers, 5'- or 3'-upstream sequences, exons, introns, etc. In other words, the action of Dbait molecules to interfere with NHEJ pathway is sequence-independent, and Dbait molecules can have less than 80% or 70%, even less than 60% or 50% sequence identity to any gene in a human genome.

This sequence-independent mechanism of action is a hallmark of Dbait molecules, which clearly distinguishes them from other gene-specific or protein-specific (sequence dependent) therapeutic agents such as antisense oligonucleotides, small interference RNA (siRNA, shRNA and miRNA), and immunostimulating CpG oligonucleotides, as well as aptamers/decoys designed to trap a specific protein.

In a preferred embodiment, the sequence of the Dbait molecules has an overall degree of identity to human nucleic acid sequences which is less than about 80%, 70%, 65%, 60%, 55% or 50%. Methods of determining sequence identity are well known in the art and include, e.g., Blast.

In a particular embodiment, the Dbait molecule does not hybridize, under stringent conditions, with human genomic DNA. Typical stringent conditions are such that they allow to discriminate fully complementary nucleic acids from partially complementary nucleic acids.

In a preferred embodiment, the sequence of the Dait molecules is devoid of CpG in order to avoid the well known toll-like receptor-mediated immunological reactions, if such effect is undesirable.

In a particular embodiment, the Dbait molecules having a double stranded portion of at least 32 pb, or of 32 bp, comprise the same nucleotide sequence than Dbait32 (SEQ ID No 1), Dbait32Ha (SEQ ID No 28), Dbait32Hb (SEQ ID No 29), Dbait32Hc (SEQ ID No 30) or Dbait32Hd (SEQ ID No 31). Optionally, the Dbait molecules have the same nucleotide composition than Dbait32, Dbait32Ha, Dbait32Hb, Dbait32Hc or Dbait32Hd but their nucleotide sequence is different. Then, the Dbait molecules comprise one strand of the double stranded portion with 3 A, 6 C, 12 G and 11 T. Preferably, the sequence of the Dbait molecules does not contain any CpG dinucleotide.

Considering their mechanism of action, the length of Dbait molecules may be variable, as long as it is sufficient to allow appropriate binding of Ku protein complex comprising Ku and DNA-PKcs proteins. The experimental section of WO2005/040378 showed that the length of Dbait molecules must be greater than 16 bp, preferably 32 bp, to ensure binding to such a Ku complex and allowing DNA-PKcs activation.

Preferably, Dbait molecules comprise between 16-200 bp, more preferably 24-100 bp, still more preferably 26-100, and most preferably between 32-100 bp. For instance, Dbait molecules comprise between 24-160, 26-150, 28-140, 30-120, 32-100 bp. By "bp" is intended that the molecule comprise a double stranded portion of the indicated length.

In a particular embodiment, the double stranded portion comprises at least 16, 18, 20, 22, 24, 26, 28, 30 or 32 consecutive nucleotides of Dbait32 (SEQ ID No 1), Dbait32Ha (SEQ ID No 28), Dbait32Hb (SEQ ID No 29), Dbait32Hc (SEQ ID No 30) or Dbait32Hd (SEQ ID No 31). In a more particular embodiment, the double stranded portion consists in 16, 18, 20, 22, 24, 26, 28, 30 or 32 consecutive nucleotides of Dbait32 (SEQ ID No 1), Dbait32Ha (SEQ ID No 28), Dbait32Hb (SEQ ID No 29), Dbait32Hc (SEQ ID No 30) or Dbait32Hd (SEQ ID No 31).

The Dbait molecules according to the invention must have at least one free end, as a mimic of DSB. Said free end may be either a free blunt end or a 5'-/3'-protruding end. In a particular embodiment, they contain only one free end. In another particular embodiment, they contain two free ends. Accordingly, the present invention also concerns Dbait molecules being a double stranded molecule with two free ends and having the nucleotide sequence of Dbait32 (SEQ ID No 1), Dbait32Ha ds (SEQ ID No 28), Dbait32Hb ds (SEQ ID No 29), Dbait32Hc ds (SEQ ID No 30) or Dbait32Hd ds (SEQ ID No 31).

Dbait molecules can be linear or, preferably, made of hairpin double-stranded nucleic acids. In such a case, the loop can be nucleic acids, or other chemical groups known by skilled person, preferably a linker such as hexaethyleneglycol or tetradeoxythymidylate (T4). Accordingly, in a particular embodiment, the Dbait molecules can be a hairpin molecule having a double stranded portion comprising at least 16, 18, 20, 22, 24, 26, 28, 30 or 32 consecutive nucleotides of Dbait32 (SEQ ID No 1), Dbait32Ha (SEQ ID No 28), Dbait32Hb (SEQ ID No 29), Dbait32Hc (SEQ ID No 30) or Dbait32Hd (SEQ ID No 31) and a loop being a hexaethyleneglycol linker or a tetradeoxythymidylate linker (T4). In a more particular embodiment, those Dbait molecules can have a double stranded portion consisting in 16, 18, 20, 22, 24, 26, 28, 30 or 32 consecutive nucleotides of Dbait32 (SEQ ID No 1), Dbait32Ha (SEQ ID No 28), Dbait32Hb (SEQ ID No 29), Dbait32Hc (SEQ ID No 30) or Dbait32Hd (SEQ ID No 31).

In a preferred embodiment, the Dbait molecules are such that:

1) the double-stranded Dbait molecules are capable of being uptaken by cells/tissue body into the cell nucleus when used with pharmaceutically acceptable carriers/excipients;

2) at least one free end of the Dbait molecules is recognizable by the holocomplex of enzymes involved in DSB damage sensing, signaling and/or repair processes; and, 3) at least one free end of the Dbait molecules is amenable by said complex to be incorporated in the tumor cell genomic DNA.

In a particular embodiment, the Dbait molecules have a non replicative structure, due their structure such as a loop, and/or backbone.

In this respect, the Dbait molecules according to the invention may have exclusively or mainly (above 50%) a native phosphodiester backbone or a chemically modified phosphodiester backbone, or another backbone with chemical groups or mixtures of chemical groups, provided the modified dsDNA remain substrates for the holocomplex involved in the NHEJ pathway, particularly Ku and DNA-PKcs proteins, as well as DSB damage sensing or signaling pathway. Advantageously, the chemical modifications are intended to confer chemical stability to Dbait molecules and/or to prevent them for further replication (potential cause of mutagenic effect) upon their genomic integration if it occurs.

In a preferred embodiment, the Dbait molecules comprise a 2'-deoxynucleotide backbone, and optionally comprise one or several (2, 3, 4, 5 or 6) modified nucleotides and/or nucleobases other than adenine, cytosine, guanine and thymine. Accordingly, the Dbait molecules are essentially a DNA structure.

They can also have sugar mimics such as 2'-O-alkylribose, 2'-O-alkyl-C4' branched ribose, cyclobutyls or other carbocyclics or hexitol in place of the pentofuranosyl group.

Preferred Dbait comprise one or several chemically modified nucleotide(s) or group(s) at the end of one or of each strand. In a particular preferred embodiment, the free end(s) of the Dbait molecules is(are) protected by one, two or three modified phosphodiester backbones at the end of one or of each strand. Preferred chemical groups, in particular the modified phosphodiester backbone comprise phosphorothioates. Alternatively, preferred Dbait have 3'-3' nucleotide linkage, or nucleotides with methylphosphonate backbone.

Other modified backbones of the invention comprise phosphoramidates, morpholino nucleic acid, 2'-0,4'-C methylene/ethylene bridged locked nucleic acid, peptide nucleic acid (PNA), and short chain alkyl, or cycloalkyl intersugar linkages or short chain heteroatomic or heterocyclic intrasugar linkages of variable length, or any modified nucleotides known by skilled person.

U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phophodiester backbone of the oligonucleotide may be replaced with a polyamide backbone, the bases being bound directly or indirectly to the aza nitrogen atoms of the polyamide backbone. Other synthetic oligonucleotides may contain substituted sugar moieties comprising one of the following at the 2' position: OH, SH, $OCH_3$, $SCH_3$, F, OCN, $OCH_2CH_2OCH_3$, $O(CH_2)_n$ $NH_2$ or $O(CH_2)$ $nCH_3$ where n is from 1 to about 10; C1 to C10 lower alkyl, substituted lower alkyl, alkaryl or aralkyl Cl; Br; CN; $CF_3$; $OCF_3$; O—S—; or N-alkyl ; O—, S—, or N-alkenyl; $SOCH_3$; $SO_2CH_3$; ONO; NO; $N_3$.

The Dbait molecule can comprise at least one embedded element, which hampers DNA replication, DNA repair, or damage signalling process. Said embedded element(s) can be incorporated at the internal position (e.g., in the centre) or at the end of the double-stranded fragment. It (they) may comprise: a) a unit which cannot be used as a template for DNA replication, such as a polyethyleneglycol chain, preferably a hexaethyleneglycol chain, or any hydrocarbon chain, eventually interrupted and/or substituted by one or more heteroatoms e.g. oxygen, sulfur, nitrogen, or heteroatomic or heterocyclic groups comprising one or more of heteroatoms; b) a unit which is a blocking element as it is not amenable by DNA polymerases or exonucleases, such as any 3'-modified nucleotides, or other ones known by skilled person; c) a native oligonucleotide, such as Tn, when used in the loop of an hairpin fragment, such as a tetradeoxythymidylate (T4).

Said strands are made by chemical synthesis, semi-biosynthesis or biosynthesis, any method of amplification, followed by any extraction and preparation methods and any chemical modification.

As disclosed in the patent application WO2005/040378, the bioactivity of Dbait molecules can be assessed by in vitro and cultured cell based assays, as described e.g., in examples 2 and 3, and/or also by in vivo assays, as described e.g., in examples 4 and 5. The most easy and relevant assay is the DNA-dependent protein kinase activity assay (cf. example 2, FIG. 1.4). This simple assay has been so far predictive of in vivo activity of Dbait molecules. However, other cultured cell based assays, such as the assay of the inhibition of radiation-enhanced illegitimate integration is also relevant (cf. example 3, FIG. 2.3 & FIG. 2.4).

Indeed, the Dbait molecules of the present invention have to be capable of activating DNA-PK. In one embodiment, the Dbait molecules are also capable of inhibiting radiation-enhanced illegitimate DNA integration. In another particular embodiment, the Dbait molecules bind a Ku complex in vitro, e.g., as determined by gel shift assay. Such a Ku complex comprises a combination of one or several Ku proteins and at least a DNA-PKc protein. In a further particular embodiment, the Dbait molecules of this invention penetrate the nucleus, preferably by using pharmaceutically acceptable carriers/excipients. Most preferred Dbait molecules of this invention combine several or all of the above characteristics.

In a preferred embodiment, the Dbait molecules are chemically modified Dbait molecules such as above defined and other practice in human therapy. In another embodiment, the Dbait molecules are not chemically modified and correspond to native nucleic acid fragments, but exhibit the characteristics of chemically modified fragments, particularly have the number of base pairs and properties defined with respect to said chemically modified Dbait molecules.

The present invention concerns the use of any Dbait molecule disclosed in the specification. In a preferred embodiment, Dbait molecule is selected from the group consisting of Dbait32 (SEQ ID No 1), Dbait32H-po (SEQ ID No 3), Dbait32H (SEQ ID No 4), Dbait32-T4 (SEQ ID No 2), Dbait32Hc-5'5' (SEQ ID No 14), Dbait32-NH2 (SEQ ID No 15), Dbait32H-FITC (SEQ ID No 21), Dbait32H-Cy3 (SEQ ID No 22), Dbait32H-Biot (SEQ ID No 23), Dbait32Ha (SEQ ID No 8), Dbait32Hb (SEQ ID No 9), Dbait32Hc (SEQ ID No 10), Dbait32Hd (SEQ ID No 11), Dbait32Hc-3'mp (SEQ ID No 12), Dbait32Hc-5'3'mp (SEQ ID No 13), Dbait32Hc-Cy3 (SEQ ID No 25), Dbait32Hc-Cy5 (SEQ ID No 26), Dbait32Hd-FITC (SEQ ID No 27), Dbait32Ha ds (SEQ ID No 28), Dbait32Hb ds (SEQ ID No 29), Dbait32Hc ds (SEQ ID No 30), Dbait32Hd ds (SEQ ID No 31), Dbait64 (SEQ ID No 19) and Dbait64L (SEQ ID No 20). A combination thereof can also be used.

Accordingly, the invention relates to a method for treating a proliferative disorder in absence of any direct or indirect DNA damaging treatment (i.e., chemo- and radio-therapies) comprising, introducing into cells and/or tissue having a proliferative disorder Dbait molecules such as above defined; thereby inducing cell lethality of said cells and/or tissue.

The present invention also relates to a method for increasing the phosphorylation of histone H2AX or for activating histone H2AX in cells and/or tissue, comprising introducing into said cells and/or tissue Dbait molecules such as above defined, thereby increasing the phosphorylation of histone H2AX and activating histone H2AX. Histone H2AX is a protein well-known by the man skilled in the art. The reference number in Swiss-Prot is P16104 and the Unigene is Hs477879. The phosphorylation is performed on Ser-139 (Li et al. 2005, for review).

The present invention relates in addition to a method for inducing cell lethality of cells and/or tissue having a proliferative disorder in absence of any direct or indirect DNA damaging treatment comprising, introducing into said cells and/or tissue Dbait molecules such as above defined; thereby inducing cell lethality of said cells and/or tissue.

In a particular embodiment of the above methods, a transfection agent is used in said introduction step. For example, the transfection agent can be selected from the group consisting of PEI (U.S. Pat. No. 6,013,240), Superfect (Qiagene), cationic lipids such as Lipofectin (Invitrogen).

In the methods and uses of the present invention, Dbait molecules are used in an efficient amount. In particular, the amount of Dbait molecules allows the molecules to reach the nuclei of the treated cells. In addition, the amount is enough to activate DNA-PK and to increase the phosphorylation of histone H2AX and to activate it.

The present invention concerns the use of Dbait molecules for preparing a medicament for treating a proliferative disorder in absence of any direct or indirect DNA damaging treatment.

In a preferred embodiment, said Dbait molecules comprise a double stranded portion of at least 16, 18, 20, 22, 24, 26, 28 or 30 bp, preferably 32 bp, have at least one free end, and wherein said Dbait molecule is substrate for binding by at least a Ku protein and are able to activate DNA-PKcs. The Dbait molecules are essentially DNA.

The present invention also relates to a method for treating a proliferative disorder in a subject, in absence of any direct or indirect DNA damaging treatment, comprising administering to said subject a therapeutically efficient amount of Dbait molecules.

In particular, the invention relates to a method for increasing the survival time of a subject suffering of a cancer in absence of any direct or indirect DNA damaging treatment (i.e., chemo- and radio-therapies) comprising, administering to said subject an therapeutically efficient amount of Dbait molecules such as above defined; thereby increasing the survival time of said subject.

The subject can be a mammal or a human. Preferably, the subject is a human. Generally, a "mammal" refers to any animal classified as a mammal including laboratory, domestic, farm and zoo animals, specifically pet animals, such as mouse, rat, rabbit, pig, sheep, goat, cattle, horse and higher primates.

Such a method relates a new therapeutic agent which can be used to treat the diseases resulting from uncontrolled cell proliferation, in particular cancer. Although Dbait is mainly intended to be used in anticancer therapies as an alternative of conventional DNA damaging therapies, it may also be used in antiproliferation treatments for non malignant diseases, such as diseases associated with too high cell division rate (proliferation), for example psoriasis or stenosis/restenosis. The antiproliferation activity has been assessed by injecting the Dbait molecules in zebrafish embryo cells at early stage. Dbait molecules specifically kill internal cells dividing rapidly and have little effect on peripheral cells dividing slowly.

The invention may be used to treat as a standalone cancer treatment of various types of cancers in mammalian subjects, particularly in human subjects, such as solid cancers and leukemia, particularly radio- or chemo-resistant cancers. The concerned organ or region can be: lung and bronchi, head and neck, brain, gastro-intestinal tract, pancreas, liver, colorectal cancer, genito-urinary tract, gynecologic organs, breast, endocrines, skin, retina, CNS, hematological organs, metastasis of known or unknown primary site, and remnants (thymus for instance). Histological nature can be epithelial, squamous cell carcinoma, adenocarcinoma, transitional carcinoma, fibroblast/angioblast derived (sarcomas), neuronal, glial derived, endocrine, carcinoid, gastrointestinal stroma, endothelial, hematopoietic, and embryonic. Preferably, the cancer is selected from the group consisting of glioblastoma, head and neck, colon, liver, lung, skin, breast cancer and cervical cancer.

The Dbait molecules can be administrated by any appropriate route, with appropriate acceptable carrier/excipient, such as oral, or intravenous, or intratumoral administration, or sub-cutaneous injections, or topic administration, or others. According to an embodiment of the invention, a transfection agent is used in combination with the Dbait molecules.

Based on the protocol used in in vivo studies, the invention provides rational to establish clinical protocol of the use of Dbait molecules. It will be easily adapted for humans by the one skilled in the art, particularly depending on the weight/body surface of the patient.

The composition according to the present invention comprises the Dbait molecules in an efficient amount to be introduced in the nucleus of tumor cells. For instance, when the intratumoral administration is used, the said efficient amount is at least 0.1 mg per 1 $cm^3$ of tumor, preferably 0.6 mg per 1 $cm^3$ of tumor, most preferably 1 mg per 1 $cm^3$ of tumor. The efficient amount can be administered in a daily treatment protocol (e.g., 5 days by week for 3 consecutive weeks or 3 times a week for 5 consecutive weeks). Alternatively, an efficient amount of at least 0.3 mg per 1 $cm^3$ of tumor, preferably 1.8 mg per 1 $cm^3$ of tumor, most preferably 3 mg per 1 $cm^3$ of tumor, can be administered in a weekly treatment protocol for 5 consecutive weeks, for instance. When other administration routes are used, the one skilled in the art can adapt the amount in order to obtain an efficient amount of the Dbait molecules in the tumor of at least 0.1 mg per 1 $cm^3$ of tumor, preferably 0.6 mg per 1 $cm^3$ of tumor, most preferably 1 mg per 1 $cm^3$ of tumor, in particular in a daily treatment protocol, or to obtain an efficient amount of the Dbait molecules in tumor of at least 0.3 mg per 1 $cm^3$ of tumor, preferably 1.8 mg per 1 $cm^3$ of tumor, most preferably 3 mg per 1 $cm^3$ of tumor, in particular in a weekly treatment protocol.

In addition, the present invention also relates to histone H2AX as a marker of the efficiency of a treatment of a proliferative disorder (e.g., a cancer), in particular by Dbait molecules as described herein. Then, the present invention relates to a method for assessing the efficiency of a treatment with Dbait molecules comprising determining the phosphorylation rate of histone H2AX. The phosphorylation of histone H2AX can be detected for instance as described in the Examples. A higher phosphorylation level of histone H2AX in comparison with the phosphorylation level without any treatment is indicative of the efficiency of the treatment. In particular, the method comprises, administering Dbait molecules to a subject, determining a phosphorylation level of histone H2AX, and comparing the determined phosphorylation level of histone H2AX with and without any treatment by Dbait molecules.

A constitutive high level of phosphorylated histone H2AX before any treatment in a specific tumor is also a good marker of the efficiency of a Dbait standalone treatment on this tumor.

Others characteristics and advantages of the invention will be given in the following examples, with reference to the attached figures and Tables.

EXAMPLES

Although the Dbaits molecules were fully described in the patent application WO2005/040378, for the sake of clarity, the design, synthesis and preparation of Dbait molecules is summarized in the example 1.

Molecular and cellular studies on the capacity of inducing phosphorylation of H2AX, as well as the demonstration of involvement of DNA-PKcs, and non involvement of ATM-mediated pathway are shown in the example 2.

In vivo assays which show tumor regression and prolongated survival in xenografted human tumors on nude mice are described in example 3.

Example 1

Design, Synthesis and Preparation of Dbait Molecules

Two types of Dbait molecules were designed: linear or hairpin dsDNA fragments. For hairpin Dbait molecules, a hexaethyleneglycol linker or a tetradeoxythymydylate was used as loop.

The end(s) of dsDNA stem can be protected against chemical degradation by 3'-exonucleases by the incorporation of phosphorothioates, methylphosphonates or 3'-3'nucleotide linkage. In principle, other chemical modifications can be used provided that they are compatible with Ku70/Ku80 binding and DNA-PKcs activation (Martensson & Hammarten, 2002). Different Dbait molecules with various stem length 8 bp (Dbait8H), 16 bp (Dbait16H), 24 bp (Dbait24H) and 32 bp (Dbait32H), as well as different stem sequences with similar GC/AT contents (Dbait32H, Dbait32Ha, Dbait32Hb, Dbait32Hc and Dbait32Hd) were synthesized and assayed. It is worth noticing the absence of CpG sequences in Dbait32Hc. A dumbell dsDNA fragment (Dbait32C) where both ends were sealed by two hexaethylene loops was also designed, as control. Some Dbait molecules were labelled via a T tagged with fluorescein (Dbait32H-FITC), cyanine 3(Dbait32H-Cy3), cyanine 5 (Dbait32Hc-Cy5), or biotin (Dbait32H-Biot). Table 1, 2 and 3 summarized the sequences and chemical structures of Dbait molecules used in this work.

Dbait molecules are disclosed in the sequence listing under the following reference number : Dbait32 (SEQ ID No 1), Dbait32-T4 (SEQ ID No 2), Dbait32H-po (SEQ ID No 3), Dbait32H (SEQ ID No 4), Dbait24H (SEQ ID No 5), Dbait16H (SEQ ID No 6), Dbait8H (SEQ ID No 7), Dbait32Ha (SEQ ID No 8), Dbait32Hb (SEQ ID No 9), Dbait32Hc (SEQ ID No 10), Dbait32Hd (SEQ ID No 11), Dbait32Hc-3'mp (SEQ ID No 12), Dbait32Hc-5'3'mp (SEQ ID No 13), Dbait32Hc-5'5' (SEQ ID No 14), Dbait32-NH2 (SEQ ID No 15), Dbait32C (SEQ ID No 16), Dbait32ss (SEQ ID No 17), Dbait32Hcss-po (SEQ ID No 18), Dbait32Ha ds (SEQ ID No 28), Dbait32Hb ds (SEQ ID No 29), Dbait32Hc ds (SEQ ID No 30), Dbait32Hd ds (SEQ ID No 31), Dbait32H-FITC (SEQ ID No 21), Dbait32H-Cy3 (SEQ ID No 22), Dbait32H-Biot (SEQ ID No 23), Dbait32Hc-Cy3 (SEQ ID No 25), Dbait32Hc-Cy5 (SEQ ID No 26), Dbait32Hd-FITC (SEQ ID No 27), Dbait64 (SEQ ID No 19) and Dbait64L (SEQ ID No 20).

TABLE 1.1

Sequences and chemical structures of Dbait molecules.

| Dbait molecules | Sequences and chemical structures |
|---|---|
| Dbait32 | 5'ACGCACGGGTGTTGGGTCGTTTGTTCGGATCT3'<br>3'TGCGTGCCCACAACCCAGCAAACAAGCCTAGA5' |
| Dbait32-T4 | 5'ACGCACGGGTGTTGGGTCGTTTGTTCGGATCT ⎞<br>3'TGCGTGCCCACAACCCAGCAAACAAGCCTAGA ⎠T₄ |
| Dbait32H-po | 5'ACGCACGGGTGTTGGGTCGTTTGTTCGGATCT3'⎞<br>3'TGCGTGCCCACAACCCAGCAAACAAGCCTAGA5'⎠ |
| Dbait32H | 5'ACGCACGGGTGTTGGGTCGTTTGTTCGGATCT3'⎞<br>3'TGCGTGCCCACAACCCAGCAAACAAGCCTAGA5'⎠ |
| Dbait24H | 5'ACGCACGGGTGTTGGGTCGTTTGT3'⎞<br>3'TGCGTGCCCACAACCCAGCAAACA5'⎠ |
| Dbait16H | 5'ACGCACGGGTGTTGGG3'⎞<br>3'TGCGTGCCCACAACCC5'⎠ |
| Dbait8H | 5'ACGCACGG3'⎞<br>3'TGCGTGCC5'⎠ |
| Dbait32Ha | 5'CGTAGGTCTGTTTGGTGGCTTTGCAGTGGCAC3'⎞<br>3'GCATCCAGACAAACCACCGAAACGTCACCGTG5'⎠ |
| Dbait32Hb | 5'GCTAGGTCTGTTTGGTGGCTTTGCAGTGGCAC3'⎞<br>3'CGATCCAGACAAACCACCGAAACGTCACCGTG5'⎠ |
| Dbait32Hc | 5'GCTGTGCCCACAACCCAGCAAACAAGCCTAGA3'⎞<br>3'CGACACGGGTGTTGGGTCGTTTGTTCGGATCT5'⎠ |
| Dbait32Hd | 5'GCTAGGTCTGTTTGGTGGCTTTGCAGTGGCAC3'⎞<br>3'CGATCCAGACAAACCACCGAAACGTCACCGTG5'⎠ |
| Dbait32a | 5'CGTAGGTCTGTTTGGTGGCTTTGCAGTGGCAC3'<br>3'GCATCCAGACAAACCACCGAAACGTCACCGTG5' |
| Dbait32b | 5'GCTAGGCTTGTTTGCTGGGTTGTAGGCACAGC3'<br>3'CGATCCGAACAAACGACCCAACATCCGTGTCG5' |
| Dbait32c | 5'GCTGTGCCCACAACCCAGCAAACAAGCCTAGA3'<br>3'CGACACGGGTGTTGGGTCGTTTGTTCGGATCT5' |
| Dbait32d | 5'GCTAGGTCTGTTTGGTGGCTTTGCAGTGGCAC3'<br>5'CGATCCAGACAAACCACCGAAACGTCACCGTG5' |
| Dbait32Hc-3'mp | 5'GCTGTGCCCACAACCCAGCAAACAAGCCTAGA3'⎞<br>3'cgaCACGGGTGTTGGGTCGTTTGTTCGGATCT5'⎠ |
| Dbait32Hc-5'3'mp | 5'gctGTGCCCACAACCCAGCAAACAAGCCTAGA3'⎞<br>3'cgaCACGGGTGTTGGGTCGTTTGTTCGGATCT5'⎠ |
| Dbait32Hc-5'5' | 5'GCTAGGCTTGTTTGCTGGGTTGTAGGCACAGC3'⎞<br>5'C3'-3'GATCCGAACAAACGACCCAACATCCGTGTCG5'⎠ |
| Dbait32-NH2 | 5'ACGCACGGGTGTTGGGTCGTTTGTTCGGATCT3'-NH₂<br>3'TGCGTGCCCACAACCCAGCAAACAAGCCTAGA5'-NH₂ |
| Dbait32C | ⎛5'ACGCACGGGTGTTGGGTCGTTTGTTCGGATCT3'⎞<br>⎝3'TGCGTGCCCACAACCCAGCAAACAAGCCTAGA5'⎠ |
| Dbait32ss | 5'ACGCACGGGTGTTGGGTCGTTTGTTCGGATCT-3' |
| Dbait32Hcss-po | 5'GCTGTGCCCACAACCCAGCAAACAAGCCTAGA3' |

The uppercase letters are nucleotides with phosphodiester backbone. The bold uppercase letters are nucleotides with phosphorothioate backbone. Half circle solid line symbolizes hexaethyleneglycol linker. Dbait32-T4 contains four thymines (T₄) as a linker instead of a hexaethyleneglycol linker. Dbait32C is a dumbbell (closed) molecule. Dbait32Hc-5'5' is derived from Dbait32Hc where a 3'-3' linkage was introduced at the previously 3'-end, thus presenting only two 5'-ends.

TABLE 1.2

Sequences and chemical structures of various labelled Dbait molecules as indicated.

| Dbait molecules | Sequences and chemical structures |
|---|---|
| Dbait32H-FITC<br>Dbait32H-Cy3<br>Dbait32H-Biot | 5'ACGCACGGGTGTTGGGTCGTTTGTTCGGATC*t*3'⎤<br>3'TGCGTGCCCACAACCCAGCAAACAAGCCTAGA5'⎦<br>*t* = fluorescein (FITC), cyanine 3 (Cy3) or biotin (Biot)-tagged T |
| Dbait8Hc-Cy3 | 5'GCTGTGCA3'⎤<br>3'CGACACG*t*5'⎦<br>*t* = cyanine 3 (Cy3)-tagged T |
| Dbait32Hc-Cy3<br>Dbait32Hc-Cy5 | 5'GCTGTGCCCACAACCCAGCAAACAAGCCTAGA3'⎤<br>3'CGACACGGGTGTTGGGTCGTTTGTTCGGATC*t*5'⎦<br>*t* = cyanine 3 (Cy3) or Cyanine 5 (Cy5)-tagged T |
| Dbait32Hd-FITC | 5'GCTAGGTCTGTTTGGTGGCTTTGCAGTGGCAC3'⎤<br>3'CGATCCAGACAAACCACCGAAACGTCACCG*t*G5'⎦<br>*t* = fluorescein (FITC)-tagged T |

TABLE 1.3

Sequences and chemical structures of 64-bp Dbait64 and Dbait64L molecules. The uppercase letters are nucleotides with phosphodiester backbone. The bold uppercase letters are nucleotides with phosphorothioate backbone. Solid line symbolizes a hexaethyleneglycol linker.

| Dbait molecules | Sequences and chemical structures |
|---|---|
| Dbait64 | 5'ACGCACGGGTGTTGGGTCGTTTGTTCGGATCTACGCA<br>CCGGTCGTTTGTTCGGTGTTGGCGATCT3'<br><br>3'TGCGTGCCCACAACCCAGCAAACAAGCCTAGATGCGT<br>GCCAGCAAACAAGCCACAACCGCTAGA5' |
| Dbait64L | 5'ACGCACGGGTGTTGGGTCGTTTGTTCGGATCT—AC<br>GCACGGTCGTTTGGTCGGTGTTGGCGATCT3'<br><br>3'TGCGTGCCCACAACCCAGCAAACAAGCCTAGA—TG<br>CGTGCCAGCAAACAAGCCACAACCGCTAGA5' |

All Dbait molecules were made by automate solid phase oligonucleotide synthesis (Eurogentec, Belgium). They were purified by denaturing reverse phase HPLC. Denaturing capillary gel electrophoresis. MALDI-TOF/LC-MS were used for quality control. More than 85% or 90% of oligonucleotides are full length. All samples were lyophilized before shipping.

Upon reception, all samples were dissolved in bi-distilled water. The concentrations of Dbait molecules were calculated from absorbance at 260 nm (Cantor et al., 1970) under denaturing condition (60° C.-90° C. depending on the thermal stability of Dbait molecules). The concentrations of fluorescent dye tagged Dbait molecules were calculated from absorbance at the appropriate wavelength of the particular dye (FITC: $\epsilon$=80000 $M^{-1}.cm^{-1}$ at 490 nm; Cy3: $\epsilon$=150000 $M^{-1}.cm^{-1}$ at 550 nm; Cy5: $\epsilon$=250000 $M^{-1}.cm^{-1}$ at 650 nm). The dumbell dsDNA fragment (Dbait32C) was prepared by annealing and ligation by DNA T4 ligase (BioLabs) of two semi hairpins carrying hexaethyleneglycol linker and with 3'-protruding and complementary ends.

Based on the thermodynamic and kinetic considerations, the following protocols were used for preparing the samples of Dbait molecules, according to their molecularity:

For Bi-molecular Dbait Molecules (Dbait32, Dbait32-NH2, Dbait64 and Dbait64L):

The mixture of 1:1 stock solution (preferably at high concentration) of each strand in bi-distilled water has to be heated at 90° C. for 5 minutes for complete denaturation of each strand. The annealing was carried out by smooth return to room temperature (the samples are typically left in water bath) and the resulting duplex molecules were stored in aliquot at −20° C.

For Mono-molecular Dbait Molecules (Hairpin):

The solution containing 200 μM of hairpin Dbait molecules in bi-distilled water has to be heated at 90° C. for 5 minutes for complete denaturation. The annealing has to be carried out by chilling the samples into ice-water (0° C.). Storage of aliquots was at −20° C.

Example 2

Molecular and Cellular Bioactivities of Dbait Molecules Per Se

The patent application WO2005/040378 provided evidence that in the presence of cell crude extract and in the absence of any DNA damaging treatment:

1) Dbait molecules are baits for Ku proteins involved in the first step of NHEJ pathway;

2) Dbait molecules are competitors of DNA end-joining reaction, but do not displace the bound complex. The recruitment of Ku proteins is a pre-request;

3) 32-bp long Dbait molecules are able to activate DNA-PK. A simple cell free DNA-PK activity assay points out that only the length (about 32-bp) and the double stranded DNA with a free end of Dbait molecules are required for the kinase activation, regardless their sequence and chemical modifications to some extent. This is consistent with the implication of DNA-PKcs in the NHEJ pathway, a sequence independent DNA end joining mechanism.

Further experiments have been carried out by the inventors to assess if Dbait molecules have biological impacts in the absence of any DNA damaging treatment. It has been surprisingly found that the presence of Dbait molecules induces the phosphorylation of a variant of histone, H2AX, known as the guardian of genome integrity, as the phosphorylated form of H2AX, γ-H2AX, forms foci at DSB sites, and triggers downstream DNA repair. The extent of γ-H2AX in either cultured cells or cells collected in tumors treated by Dbait32Hc is analyzed by western blot and FACS. In vivo, significant tumor regression is observed in three xenografted human tumors on nude mice.

Established human cell lines Hep2 (head and neck squamous cell carcinoma, HNSCC), LU1205 and SK28 (melanomas) were used for animal studies. Studies of cells in culture were performed using Hep2, HeLa S3 (epithelia cervical carcinoma), MO59K and MO59J (glioblastoma), MRC5 and AT5BI (fibroblast). Cells were grown at 37° C. in monolayer cultures in complete DMEM containing 10% heat-inactivated fetal bovine serum (FBS; Invitrogen, Cergy Pontoise, France) and antibiotics (100 μg/ml streptomycin and 100 μg/ml penicillin) under conditions of 100% humidity, 95% air and 5% $CO_2$. LU1205 were grown in MCDB containing 4% heat-inactivated FBS, 1% glutamine and antibiotics (100 μg/ml streptomycin and 100 μg/ml penicillin).

Exponentially growing cells in six-well plates were harvested and incubated with 700 ml of complete DMEM containing a mixture of Dbait molecules and Superfect reagent (Qiagen, Courtaboeuf, France) in a ratio of 10 μl Superfect per µg DNA. After 5 h at 37° C. under standard conditions, the cells were washed with PBS and complete DMEM was added.

For Western blot analysis, the cells were grown in 5 cm diameter Petri dishes, 2 µg Dbait32Hc molecules were transfected with Superfect (Qiagene) according to the manufacturer's instruction, then rest for various times in the medium at 37° C. After 5 h at 37° C. under standard conditions, the cells were washed 3 times with PBS and complete DMEM was added. Cells were incubated one additional hour, washed 3 times and lysed in Laemmli buffer. Proteins were transferred to nitrocellulose membranes, which were blocked with 5% nonfat milk (1 hour) before overnight incubation with anti-H2AX (Cell Signaling Technology, Denver, USA) and a mouse anti-phospho-Histone H2AX (Ser139) (Upstate, Tempcula, Calif., USA), rabbit monoclonal anti-phospho-Thr68-Chk2 (Cell Signaling Technology, Denver, USA), diluted 1/100 in 1× PBS,1% BSA. Blots were then incubated with horseradish peroxidase-conjugated goat anti-rabbit IgG secondary antibodies (P0448, Dako) diluted 1/5000 in TBST. Protein-antibody complexes were revealed on hyperfilm (Amersham) and quantified using ImageJ (Public domain).

For immunofluorescent detection by FACS of γ-H2AX, the cells were grown in 5 cm diameter Petri dishes, 2 µg Dbait32Hc molecules were transfected with Superfect (Qiagene) according to the manufacturer's instruction, then rest for various times in the medium at 37° C. After 3 washing cycles, the cells were fixated with 2% PFA for 10 minutes. After one additional washings, the presence of γ-H2AX was detected with rabbit anti-γ-H2AX antibody (4411-PC, Trevigen) diluted 1/100 in 1× PBS, 1% BSA. Cells were washed three times with 1× PBS, 0.5% TritonX-100, then incubated for 1 hour at room temperature with rhodamine-conjugated goat anti-rabbit antibodies diluted 1/100 in 1× PBS, 1% BSA. Cells were analyzed by FACScan flow cytometer (FACSalibur, Beckton-Dickinson, USA).

As Dbait32H/Dbait32Hc activated the kinase activity of DNA-PKcs in crude extracts, the inventors wondered whether it would induce phosphorylation of downstream targets of DNA-PKcs in living cells. The inventors therefore analyzed phosphorylation of H2AX in Dbait32Hc-transfected cells (Chowdhury et al., 2000; Paull et al. 2000).

FIG. 1 shows that transfection by Dbait32Hc highly stimulates phosphorylation of H2AX in all DNA-PKcs competent tumor cell lines (Hela, Hep2, MO59K and transformed fibroblast line MRC5). However, the phosphorylation of H2AX is not observed in DNA-PKcs deficient tumor cell line (MO59J derived from MO59K), whereas it is in DNA-PKcs competent but ATM-deficient transformed fibroblast line (AT5BI derived from MRC5). This indicates that, in vitro, Dbait-dependent kinase activation is a general process that does not depend upon the origin of the cell line. The phosphorylation of H2AX depends on the status of DNA-PKcs, but not on that of ATM. The high level of γ-H2AX lasts up to 24-48 h.

FIG. 2 shows the level of the phosphorylated form of H2AX and of the check point protein Chk2 by ATM on Thr68 (Chk2-T68p) in Hep2 cells 5 hours after various Dbait molecules transfection, and 1 hour after 10 Gy irradiation without Dbait32Hc transfection. The high level of γ-H2AX is only observed in the cells transfected by Dbait32Hc. This level is higher in Dbait32Hc transfected cells than in the irradiated cells. By contrast, the level of Chk2-T68p is poorly increased in Dbait32Hc transfected cells and is much higher in the irradiated cells. These results confirm that Dbait32Hc does not activate the kinase ATM.

FIG. 3 shows the level of γ-H2AX in the cells collected from the Hep2 tumors treated by 60µg Dbait32Hc (intratumoral injection, with PEI as transfection agent), and compared to the background level in Hep2 tumors without treatment. Tumors were removed 24 hours after treatment, frozen in liquid nitrogen and stored at −80° C. Before being analysed, cells were mechanically dissociated, then immuno-labeled for western blot or FACS analysis (see below). It is noted that the γ-H2AX level is quite high even in the untreated tumors, however, the level observed in tumors treated by Dbait32Hc is significantly higher.

FIG. 4 shows FACS analysis of about 10,000 cells. The high level of γ-H2AX is observed in the Hep2 cells of the tumor treated by 60 µg of Dbait32Hc, as compared to the untreated or treated by 60 µg Dbait8H used as a transfection control.

Example 3

Treatment of Xenografted Human Tumors on Nude Mice

In vivo activity of Dbait molecules, as a new molecular therapy, alternative of conventional DNA damaging therapies was assessed by using nude mice xenografted with human tumors by subcutaneous injection of radio-resistant cell lines (Hep2 derived from human head and neck squamous cell carcinoma, HNSCC; and LU1205 and SK28 derived from human melanoma).

Investigations were carried out on the mice xenografted with various human tumors in order to establish proof of concept in vivo. The xenograft was performed by injection of about 1 millions human tumor cells. The treatment started when the volume of tumor reached about 200 mm$^3$ (about 7-10 days after the inoculation of tumor cells). The size of tumor was measured 2-3 times a week. The volume of tumor was calculated ($V=2 \times a \times b^2$, where a=length, b=width). The mice were followed up to at least 150 days. When tumor volume exceeded 2 cm$^3$, the animals were sacrificed according to the animal experimentation ethic, and the time of sacrifice was considered as death time (survival end point used in Kaplan-Meier plot).

Typical assay condition consists of intratumoral injection of an appropriate preparation of 1-6 nmole Dbait molecules with transfecting agents polyethyleneimine (PEI, Polyplus Transfection). For HNSCC xenograft, injection of formulated Dbait molecules (Dbait32H or Dbait32Hc) was given every 2 days, 3 days a week for 5 weeks. For LU1205 and SK28 xenograft, the formulated Dbait32Hc molecules was injected for three consecutive days, and repeated once the next week.

FIG. 5 shows Kaplan-Meier plot of HNSCC xenografts on nude mice. Clear prolongated survival is observed for the treated arms by 60 µg (3 nmole) and 120 µg (6 nmole) Dbait32H/Dbait32Hc molecules, whereas the treatment by 60 µg (6 nmole) single strand control (Dbait32ss) is negative.

The benefit of Dbait32Hc is also seen in two other xenografted human tumors (LU1205 and SK28) on nude mice as shown in FIG. 6 and FIG. 7.

The benefit of Dbait32Hc is observed whatever the administration frequency for a given total amount. Administration can be fractionated at a frequency of 3, 2 or ideally one injection per week.

Descriptive analyses of the tumor response were performed for each treatment and each tumor type. Day 1 was the day of the first treatment session. All the animals were followed for at least 150 days or until their ethical sacrifice. Median lifetime was estimated according to the Kaplan-Meier method. TGD was calculated by subtracting the mean tumor volume quadrupling time of the control group from tumor volume quadrupling times of individual mice in each treated group. The mean TGD was calculated for each treated group using the individual measurements.

Overall survival curves were assessed by Kaplan-Meier estimates and compared using the non-parametric Log Rank test since the data do not follow a normal distribution. The analysis used S-Plus 6.2 version software (MathSoft Inc., Seattle, Wash.) and statEL (ad Science, Paris, France). A global Log Rank was first performed for each group with a same tumor type. Then treatments with Dbait were compared to the untreated control. The number of animals (n), the relative risk (RR) and the P value are reported in Table 4. All tests were considered significant at the 0.05 significance level.

TABLE 4

Statistical analysis of the efficacy of Dbait32H/Hc treatment in xenografted tumors on nude mice.

| Cell line | Dbait | Dbait concentration | Number of mice | Number of cured mice** | Median survival time (days) | *Relative risk (P value) | *Mean TGD | *STD TGD | *Range TGD | *Mean % TGD |
|---|---|---|---|---|---|---|---|---|---|---|
| Hep2 | — | — | 21 | | 49 | C | 0 | 3.8 | −5; 12 | 100 |
| Hep2 | 32H | 15 × 20 µg (1 nmole) | 10 | | 55 | 0.62 (p < 0.24) | 7 | 6.7 | −3; 17 | 168 |
| Hep2 | 32H | 15 × 60 µg (3 nmole) | 11 | 1 | 58 | 0.43 (p < $1.5.10^{-2}$) | >38 | 41.6 | −5; 139 | 459 |
| Hep2 | 32Hc | 15 × 60 µg (3 nmole) | 10 | | 128 | 0.3 (p < $1.10^{-4}$) | 34 | 21.3 | 7; 69 | 420 |
| Hep2 | 32H | 15 × 120 µg (6 nmole) | 11 | 1 | 148 | 0.2 (p < $4.43.10^{-6}$) | >56 | 38.7 | −3; 139 | 624 |
| Hep2 | 32ss | 15 × 120 µg (12 nmole) | 12 | | 46 | 0.71 (p < 0.29) | 6 | 4.9 | 0; 19 | 156 |
| LU | — | — | 21 | | 24 | C | 0 | 2.8 | −4; 4 | 100 |
| LU | 32Hc | 6 × 60 µg (3 nmole) | 10 | | 41 | 0.25 (p < $3.2.10^{-6}$) | 9 | 2.8 | 1; 12 | 207 |
| SK | — | — | 21 | | 54 | C | 0 | 8.2 | −19; 14 | 100 |
| SK | 32Hc | 6 × 60 µg (3 nmole) | 15 | | 88 | 0.29 (p < $1.45.10^{-5}$) | 16 | 15.0 | −4; 64 | 179 |

C: untreated tumor group used as reference group for statistics scoring
*TGD calculation and statistical analysis described in Materials and Methods
**Cured mice are animals surviving more than 200 days after the beginning of treatment Statistically significant benefit outcome of the Dbait32H/Dbait32Hc is observed in all xenografted human tumors. As the underlying mechanism of action of Dbait molecules and the ubiquitous NHEJ pathway in all cells, it is anticipated that this holds true for other tumors with different histology.

Example 4

Immune Response to Dbait Injections

No significant induction of any cytokine was detected with Dbait32Hc whatever the injection was intravenous or subcutaneous. The inventors estimate the immune response after injection intravenous (IV) or subcutaneous (SC) of Dbait32Hc in Balb/C mice. The levels of IL2, IL4, IL5, IL6, IL10, IL12P70, IFNγ and TNFα were measured in blood samples at various times after repeated injections of Dbait. Animals received seven injections of 120 mg (9 nmoles) of Dbait within 24 days without developing any toxicity manifestation or skin inflammation. The inventors compared the immune response to Dbait32Hc that does not contain any immunogenic CpG sequence and Dbait32H that contains four CpG. Only, Dbait32H induced a rapid response of IL6 and a more delayed response of IL12p70 (FIG. 8).

REFERENCES

Belenkov A. I.; Paiement J. P.; Panasci L. C.; Monia B. P.; Chow T. Y. An antisense oligonucleotide targeted to human Ku80 messenger RNA sensitizes MO59K malignant glioma cells to ionizing radiation, bleomycin, and etoposide but not DNA cross-linking agents. Cancer Res. (2002), 62, 5888-96.

Bouton., S.;, Kyle S.; Durkacz. B. W. Mechanisms of enhancement of cytotoxicity in etoposide and ionising radiation-treated cells by the protein kinase inhibitor wortmannin. Eur. J Cancer (2000), 36,535-41.

Cantor, C. R.; Warshaw, M. M.; Shapiro, H. Oligonucleotide interactions. III.Conformational differences between deoxy-and ribodinucleoside phosphates Biopolymers (1970), 9, 1059-77.

Chowdhury, D.; Keogh, M. C.; Ishii, H.; Peterson, C. L.; Buratowski, S.; Lieberman, J. gamma-H2AX dephosphorylation by protein phosphatase 2A facilitates DNA double-strand break repair. Mol. Cell. (2005) 20, 801-9.

Durant, S.; Karran, P. Vanillins—a novel family of DNA-PK inhibitors. Nucleic Acids Res. (2003), 31, 5501-12.

Jackson, S. P. Sensing and repairing DNA double-strand breaks. Carcinogenesis. (2002), 23, 687-96.

Kim, C. H.; Park, S. J.; Lee, S. H.; A targeted inhibition of DNA-dependent protein kinase sensitizes breast cancer cells following ionizing radiation. J; Pharmacol. Exp. Ther. (2002), 303, 753-9.

Li, A; Eirin-Lopez, J. M.; Ausio, J. H2AX: tailoring histone H2A for chromatin-dependent genomic integrity. Biochem. Cell Biol. (2005), 83, 505-15.

Li, S.; Takeda, Y.; Wragg, S.; Barrett, J.; Phillips, A.; Dynan, W. S. Modification of the ionizing radiation response in living cells byan scFv against the DNA-dependent protein kinase. Nucleic Acid Res. (2003a) 31, 5848-57.

Li, G. C.; He, F.; Shao, X.; Urano, M.; Shen, L.; Kim, D.; Borrelli, M.; Leibel, S. A.; Gutin, P. H.; Ling, C. C. Adenovirus-mediated heat-activated antisense Ku70 expression radiosensitizes tumor cells in vitro and in vivo. Cancer Res. (2003b), 63, 3268-74.

Marangoni, E.; Bay, J. O.; Verrelle, P.; Bourhis, J. Tranfert de gène pour modifier la réponse à la radiothérapie Cancer Radiother. (2000a), 4, 175-80.

Marangoni, E.; Foray, N.; O'Driscoll, M.; Douc-Rasy, S.; Bernier, J.; Bourhis, J.; Jeggo, P. A Ku80 fragment with dominant negative activity imparts a radiosensitive phenotype to CHO-K1 cells. Nucleic Acid Res. (2000b), 28, 4778-82.

Marangoni, E.; Le Romancer, M.; Foray, N.; Muller, C.; Douc-Rasy, S.; Vaganay, S.; Abdulkarim, B.; Barrois, M.; Calsou, P.; Bernier, J.; Salles, B.; Bourhis J. Transfer of Ku80 RNA antisense decreases the radioresistance of human fibroblasts. Cancer GeneTher. (2000c), 7, 339-46.

Martensson, S.; Hammarsten, O. DNA-dependent protein kinase catalytic subunit: structural requirements for kinase activity by DNA ends. J Biol. Che77i. (2002), 277, 3020-29.

Ohnishi, T.; Taki, T.; Hiraga, S.; Arita, N.; Morita, T. In vitro and in vivo potentiation of radiosensitivity of malignant gliomas by antisense inhibition of the RAD51 gene. Biochem Biophys Res Commun. (1998), 245, 319-24.

Paull, T. T.; Rogakou, E. P.; Yamazaki, V.; Kirchgessner C. U.; Gellert, M.; Bonner W. M. A critical role for histone H2AX in recruitment of repair factors to nuclear foci after DNA damage. Curr. Biol. (2000), 10, 886-95.

Peng, Y.; Zhang, Q.; Nagasawa, H.; Okayasu, R.; Liber, H. L.; Bedford, J. S. Silencing expression of the catalytic subunit of DNA-dependent protein kinase by small interfering RNA sensitizes human cells for radiation-induced chromosome damage, cell killing, and mutation. Cancer Res. (2002), 62, 6400-4.

Sak, A.; Stuschke, M.; Wurm, R.; Schroeder, G.; Sinn, B.; Wolf, G.; Budach, V. Selective inactivation of DNA-dependent protein kinase with antisense oligodeoxynucleotides: consequences for the rejoining of radiation-induced DNA double-strand breaks and radiosensitivity of human cancer cell lines. Cancer Res. (2002), 62, 6621-24.

Veuger, S. J.; Curtin, N. J.; Smith, G. C.; Durkacz, B. W. Effects of novel inhibitors of poly(ADP-ribose) polymerase-1 and the DNA-dependent protein kinase on enzyme activities and DNA repair. *Oncogene* (2004) 23, 7322-9.

Willmore, E.; de Caux, S.; Sunter, N. J.; Tilby, M. J.; Jackson, G. H.; Austin, C. A.; Durkacz, B. W. A novel DNA-dependent protein kinase inhibitor, NU7026, potentiates the cytotoxicity of topoisomerase 11 poisons used in the treatment of leukemia. *Blood*. (2004), 103, 4659-65.

Yoo, S. H.; Dynan, W. S. Characterization of the RNA binding properties of Ku protein. Biochemsitry (1998), 37, 1336-43.

What is claimed:

1. A method for treating a proliferative disorder in a subject comprising administering to said subject a therapeutically efficient amount of a nucleic acid molecule comprising a double stranded portion of at least 32 bp, having at least one free end, being substrate for binding by at least a Ku protein and being able to activate DNA-PK, and wherein said subject is not treated with an agent that causes direct or indirect DNA damage.

2. The method according to claim 1, wherein said molecule comprises between 32 and 100 bp.

3. The method according to claim 2, wherein said molecule is a linear or a hairpin nucleic acid molecule.

4. The method according to claim 3, wherein said molecule is a hairpin nucleic acid molecule and wherein the loop comprises nucleic acid or chemical groups.

5. The method according to claim 1, wherein the free end is blunt or 5'- or 3'-protruding.

6. The method according to claim 1, wherein said molecule is capable of being taken-up by a cell into the cell nucleus.

7. The method according to claim 1, wherein said molecule comprises a phosphodiester backbone or a chemically modified phosphodiester backbone, or another backbone with one or several chemical groups.

8. The method according to claim 1, wherein said molecule comprises a 2'-deoxynucleotide backbone, and optionally comprises one or several modified nucleotides and/or nucleobases other than adenine, cytosine, guanine and thymine.

9. The method according to claim 7, wherein said backbone comprises methylphosphonates, phosphoramidates, morpholino nucleic acid, 2'-O, 4'-C methylene/ethylene bridged locked nucleic acid, peptide nucleic acid (PNA), short chain alkyl, or cycloalkyl intersugar linkages or short chain heteroatomic or heterocyclic intrasugar linkages of variable length.

10. The method according to claim 8, wherein the molecule further comprises sugar mimetics.

11. The method according to claim 1, said molecule comprising one or several chemically modified nucleotide(s) at the end of each strand or, at least, at the 3' end strand.

12. The method according to claim 11, said molecule comprising one or several phosphorothioates at the end of each strand or, at least, at the 3'-end strand.

13. The method according to claim 1, said molecule further comprising at least one embedded element, which hampers DNA replication or DNA repair, said at least one element being incorporated in the centre or at the end of the double-stranded molecule.

14. The method according to claim 13, wherein said embedded element comprises:
   a) a polyethyleneglycol chain or any hydrocarbon chain, interrupted and/or substituted by one or more heteroatoms or heteroatomic or heterocyclic groups comprising one or several heteroatoms; and/or
   b) said embedded element is a blocking element not recognized by DNA polymerases, and/or
   c) a native oligonucleotide when used in the loop of a hairpin fragment.

15. The method according to claim 1, wherein said molecule has a double stranded portion of at least 32 bp or of 32 bp of Dbait32 (SEQ ID NO: 1), Dbait32Ha (SEQ ID NO: 28), Dbait32Hb (SEQ ID NO: 29), Dbait32Hc (SEQ ID NO: 30) or Dbait32Hd (SEQ ID NO: 31).

16. The method according to claim 15, wherein said molecule is selected from the group consisting of Dbait32 (SEQ ID NO: 1), Dbait32H-po (SEQ ID NO: 3), Dbait32H (SEQ ID NO: 4), Dbait32-T4 (SEQ ID NO: 2), Dbait32Hc-5'5' (SEQ ID NO: 14), Dbait32-NH2 (SEQ ID NO: 15), Dbait32H-FITC (SEQ ID NO: 21), Dbait32H-Cy3 (SEQ ID NO: 22), Dbait32H-Biot (SEQ ID NO: 23), Dbait32Ha (SEQ ID NO: 8), Dbait32Hb (SEQ ID NO: 9), Dbait32Hc (SEQ ID NO: 10), Dbait32Hd (SEQ ID NO: 11), Dbait32Hc-3'mp (SEQ ID NO: 12), Dbait32Hc-5'3'mp (SEQ ID NO: 13), Dbait32Hc-Cy3 (SEQ ID NO: 25), Dbait32Hc-Cy5 (SEQ ID NO: 26), Dbait32Hd-FITC (SEQ ID NO: 27), Dbait32Ha ds (SEQ ID NO: 28), Dbait32Hb ds (SEQ ID NO: 29), Dbait32Hc ds (SEQ ID NO: 30), Dbait32Hd ds (SEQ ID NO: 31), Dbait64 (SEQ ID NO: 19) and Dbait64L (SEQ ID NO: 20).

17. The method according to claim 1, wherein the double stranded portion of said molecule comprises at least 16, 18, 20, 22, 24, 26, 28, 30 or 32 consecutive nucleotides of Dbait32 (SEQ ID NO: 1), Dbait32Ha (SEQ ID NO: 28), Dbait32Hb (SEQ ID NO: 29), Dbait32Hc (SEQ ID NO: 30) or Dbait32Hd (SEQ ID NO: 31).

18. The method according to claim 1, wherein said proliferative disorder is a cancer selected from glioblastoma, head and neck, colon, liver, lung, skin, breast cancer or cervical cancer.

19. The method according to claim 1, wherein the molecule is administered orally, intravenously, intratumorally, subcutaneously, intracranially or intra-arterially.

20. The method according to claim 1, wherein said molecule is used by intratumoral administration in an amount of at least 0.1 mg per 1 $cm^3$ of tumor.

* * * * *

UNITED STATES PATENT AND TRADEMARK OFFICE
CERTIFICATE OF CORRECTION

PATENT NO.        : 8,093,366 B2
APPLICATION NO.   : 12/520961
DATED             : January 10, 2012
INVENTOR(S)       : Marie Dutreix It is certified that error appears in the above-identified patent and that said Letters Patent is hereby corrected as shown below:

Column 1,
Line 32, "Despite of many" should read --Despite the many--.

Column 2,
Lines 16-17, "worth to note" should read --worth noting--.

Column 4,
Line 45, "the Dait" should read --the Dbait--.
Line 50, "at least 32 pb" should read --at least 32bp--.

Column 5,
Line 30, "by skilled" should read --by the skilled--.

Column 6,
Lines 1-2, "prevent them for" should read --prevent them from--.

Column 8,
Line 37, "suffering of a" should read --suffering from a--.

Column 9,
Line 31, "5 days by week" should read --5 days a week--.

Column 10,
Line 1, "Others characteristics" should read --Other characteristics--.

Signed and Sealed this
Twelfth Day of June, 2012

David J. Kappos
*Director of the United States Patent and Trademark Office*

CERTIFICATE OF CORRECTION (continued)
U.S. Pat. No. 8,093,366 B2

Column 11,
Table 1.1, Row Dbait32Hb, "5'GCTAGGTCTGTTTGGTGGCTTTGCAGTGGCAC3'
                      3'CGATCCAGACAAACCACCGAAACGTCACCGTG5'"
      should read
           --5'GCTAGGCTTGTTTGCTGGGTTGTAGGCACAGC3'
             3'CGATCCGAACAAACGACCCAACATCCGTGTCG5'--.

Column 13,
Table 1.3, Row Dbait64,
    "5'ACGCACGGGTGTTGGGTCGTTTGTTCGGATCTACGCACCGGTCGTTT
    GTTCGGTGTTGGCTGATCT3'"
should read
    --5'ACGCACGGGTGTTGGGTCGTTTGTTCGGATCTACGCACGGTCGTTT
    GTTCGGTGTTGGCGATCT3'--.

Table 1.3, Row Dbait64L,
    "5'ACGCACGGGTGTTGGGTCGTTTGTTCGGATCT–ACGCACGGTCGTTT
    GGTCGGTGTTGGCGATCT3'"
should read
    --5'ACGCACGGGTGTTGGGTCGTTTGTTCGGATCT–ACGCACGGTCGTTT
    GTTCGGTGTTGGCGATCT 3'--.

Column 15,
Line 29, "washings" should read --washing--.
Line 45, "(Hela," should read --(HeLa,--.

Column 16,
Line 31, "1 millons" should read --1 millon--.

Column 39,
Line 46, "centre" should read --center--.